US00RE42379E

(19) United States
(12) Reissued Patent
Loomas

(10) Patent Number: US RE42,379 E
(45) Date of Reissued Patent: May 17, 2011

(54) GAS-TIGHT SEAL ACCOMODATING SURGICAL INSTRUMENTS WITH A WIDE RANGE OF DIAMETERS

(75) Inventor: Bryan E. Loomas, Los Gatos, CA (US)

(73) Assignee: Applied Medical Resources Corporation, Rancho Santa Margarita, CA (US)

(21) Appl. No.: 11/132,741

(22) Filed: May 18, 2005

Related U.S. Patent Documents

Reissue of:
(64) Patent No.: 5,407,433
Issued: Apr. 18, 1995
Appl. No.: 08/015,765
Filed: Feb. 10, 1993

(51) Int. Cl.
*A61M 5/178* (2006.01)
*F16J 15/00* (2006.01)
*A61M 5/14* (2006.01)

(52) U.S. Cl. ..... 604/167.06; 277/505; 277/580; 604/256

(58) Field of Classification Search ..... 604/167.01–167.06, 256
See application file for complete search history.

(56) References Cited

U.S. PATENT DOCUMENTS

| | | | |
|---|---|---|---|
| 2,797,837 | A | 7/1957 | Roberts |
| 3,197,173 | A | 7/1965 | Taubenheim |
| 3,875,938 | A | 4/1975 | Mellor |
| 3,970,089 | A | 7/1976 | Saice |
| 3,977,400 | A | 8/1976 | Moorehead |
| 3,994,287 | A | 11/1976 | Turp et al. |
| 4,000,739 | A | 1/1977 | Stevens |
| 4,112,932 | A | 9/1978 | Chiulli |
| 4,177,814 | A | 12/1979 | Knepshield et al. |
| 4,177,997 | A | 12/1979 | Cartwright |
| 4,233,982 | A | 11/1980 | Bauer et al. |
| 4,240,411 | A | 12/1980 | Hosono |

(Continued)

FOREIGN PATENT DOCUMENTS

| | | |
|---|---|---|
| DE | 2845643 | 4/1980 |

(Continued)

OTHER PUBLICATIONS

Memorandum of Points and Authorities in Support of Applied's Motion for Partial Summary Judgment that Surgical Infringes U.S. Patent No. 5,407,433, Sep. 30, 1999.

(Continued)

*Primary Examiner* — Kevin C Sirmons
*Assistant Examiner* — Catherine N Witczak
(74) *Attorney, Agent, or Firm* — Knobbe Martens Olson & Bear, LLP

(57) ABSTRACT

A seal for use in a surgical instrument to provide a gas-tight seal with an instrument passed through the seal. The seal can form a gas-tight seal with an instrument having a diameter within a wide range of diameters. The seal comprises a seal body, an instrument seal, and a laterally-compliant seal mounting device. The seal body includes a bore through which the instrument is passed. The instrument seal is made of an elastic material and is disposed substantially perpendicular to the axis defined by the bore in the seal body. The instrument seal includes an instrument port through which the instrument is passed. The laterally-compliant seal mounting device mounts the instrument seal to the seal body, forms a gas-tight seal between the instrument seal and the seal body, and allows the instrument seal to move freely laterally in response to lateral movement of the instrument.

56 Claims, 9 Drawing Sheets

U.S. PATENT DOCUMENTS

| | | | | |
|---|---|---|---|---|
| 4,243,034 | A | | 1/1981 | Brandt |
| 4,338,689 | A | | 7/1982 | Zieg |
| 4,338,934 | A | | 7/1982 | Spademan |
| 4,379,458 | A | | 4/1983 | Bauer et al. |
| 4,424,833 | A | | 1/1984 | Spector et al. |
| 4,430,081 | A | | 2/1984 | Timmermans |
| 4,494,760 | A | | 1/1985 | Spargo |
| 4,512,766 | A | | 4/1985 | Vailancourt |
| 4,531,937 | A | | 7/1985 | Yates |
| 4,535,773 | A | | 8/1985 | Yoon |
| 4,540,411 | A | | 9/1985 | Bodicky |
| 4,553,760 | A | | 11/1985 | Reed et al. |
| 4,580,573 | A | | 4/1986 | Quinn |
| 4,588,195 | A | | 5/1986 | Antonini et al. |
| 4,601,710 | A | | 7/1986 | Moll |
| 4,610,665 | A | | 9/1986 | Matsumoto et al. |
| 4,610,674 | A | | 9/1986 | Suzuki et al. |
| 4,611,785 | A | | 9/1986 | Steer |
| 4,613,329 | A | | 9/1986 | Bodicky |
| 4,626,245 | A | | 12/1986 | Weinstein |
| 4,629,450 | A | | 12/1986 | Suzuki et al. |
| 4,634,432 | A | | 1/1987 | Kocak |
| 4,654,030 | A | | 3/1987 | Moll et al. |
| 4,655,752 | A | | 4/1987 | Honkanen et al. |
| 4,673,393 | A | | 6/1987 | Suzuki et al. |
| 4,705,511 | A | | 11/1987 | Kocak |
| 4,723,550 | A | | 2/1988 | Bales et al. |
| 4,759,751 | A | | 7/1988 | Gabel et al. |
| 4,798,594 | A | | 1/1989 | Hillstead |
| 4,813,938 | A | | 3/1989 | Raulerson |
| 4,842,591 | A | | 6/1989 | Luther |
| 4,857,062 | A | | 8/1989 | Russell |
| 4,869,717 | A | | 9/1989 | Adair |
| 4,874,377 | A | | 10/1989 | Newgard et al. |
| 4,874,378 | A | | 10/1989 | Hillstead |
| 4,889,349 | A | | 12/1989 | Muller |
| 4,895,346 | A | | 1/1990 | Steigerwald |
| 4,909,798 | A | | 3/1990 | Fleischhacker et al. |
| 4,917,668 | A | | 4/1990 | Haindl |
| 4,929,235 | A | | 5/1990 | Merry et al. |
| 4,932,633 | A | | 6/1990 | Johnson et al. |
| 4,935,010 | A | | 6/1990 | Cox et al. |
| 4,943,280 | A | | 7/1990 | Lander |
| 4,960,259 | A | | 10/1990 | Sunnanvader et al. |
| 4,960,412 | A | | 10/1990 | Fink |
| 4,966,588 | A | | 10/1990 | Rayman et al. |
| 4,978,341 | A | | 12/1990 | Niederhauser |
| 5,000,745 | A | | 3/1991 | Guest et al. |
| 5,002,557 | A | | 3/1991 | Hasson |
| 5,006,114 | A | | 4/1991 | Rogers et al. |
| 5,009,391 | A | | 4/1991 | Steigerwald |
| 5,030,206 | A | | 7/1991 | Lander |
| 5,041,095 | A | | 8/1991 | Littrell |
| 5,053,014 | A | | 10/1991 | Van Hevgten |
| 5,053,016 | A | | 10/1991 | Lander |
| 5,059,186 | A | | 10/1991 | Yamamoto et al. |
| 5,073,169 | A | | 12/1991 | Raiken |
| 5,098,393 | A | | 3/1992 | Amplatz et al. |
| 5,104,383 | A | | 4/1992 | Shichman |
| 5,108,373 | A | | 4/1992 | Bancsi et al. |
| 5,108,380 | A | | 4/1992 | Herlitze et al. |
| 5,127,626 | A | * | 7/1992 | Hilal et al. ..... 251/149.1 |
| 5,137,520 | A | | 8/1992 | Maxson et al. |
| 5,167,636 | A | * | 12/1992 | Clement ..... 604/167.03 |
| 5,180,373 | A | * | 1/1993 | Green et al. ..... 604/167.03 |
| 5,197,955 | A | * | 3/1993 | Stephens et al. ..... 604/167.01 |
| 5,201,714 | A | * | 4/1993 | Gentelia et al. ..... 604/167.04 |
| 5,209,736 | A | * | 5/1993 | Stephens et al. ..... 604/164.09 |
| 5,209,737 | A | * | 5/1993 | Ritchart et al. ..... 604/167.03 |
| 5,221,264 | A | * | 6/1993 | Wilk et al. ..... 604/167.01 |
| 5,226,891 | A | | 7/1993 | Bushatz et al. |
| 5,242,412 | A | | 9/1993 | Blake, III |
| 5,300,036 | A | * | 4/1994 | Mueller et al. ..... 604/167.06 |
| 5,308,336 | A | | 5/1994 | Hart et al. |
| 5,342,315 | A | | 8/1994 | Rowe et al. |
| 5,385,553 | A | | 1/1995 | Hart et al. |
| 5,407,433 | A | | 4/1995 | Loomas |
| 5,411,483 | A | | 5/1995 | Loomas et al. |
| 5,496,280 | A | | 3/1996 | Vandenbroek et al. |
| 5,545,142 | A | | 8/1996 | Stephens et al. |

FOREIGN PATENT DOCUMENTS

| | | | |
|---|---|---|---|
| EP | 29864 | | 6/1981 |
| EP | 0051718 | | 5/1982 |
| EP | 054728 | | 6/1982 |
| EP | 0113520 | | 7/1984 |
| EP | 0312219 | | 4/1989 |
| EP | 344907 | | 12/1989 |
| EP | 350291 | | 1/1990 |
| GB | 1199498 | | 7/1970 |
| GB | 1482857 | | 8/1977 |
| GB | 2019219 | | 10/1979 |
| GB | 2063679 | | 6/1981 |
| WO | WO 93/04717 | * | 3/1993 |
| WO | WO/04717 | * | 3/1993 |

OTHER PUBLICATIONS

Statement of Uncontroverted Facts and Conclusions of Law in Support of Applied's Motion for Partial Summary Judgment that Surgical Infringes U.S. Patent No. 5,407,433, Sep. 30, 1999.

Declaration of Technical Expert Dr. Barry Feinberg in Support of Applied's Motion for Partial Summary Judgment that Surgical Infringes U.S. Patent No. 5,407,433, Sep. 30, 1999.

Memorandum of Points and Authorities in Support of Applied's Motion for Partial Summary Judgment that Surgical Infringes U.S. Patent No. 5,411,483, Sep. 30, 1999.

Statement of Uncontroverted Facts and Conclusions of Law in Support of Applied's Motion for Partial Summary Judgment that Surgical Infringes U.S. Patent No. 5,411,483, Sep. 30, 1999.

Declaration of Technical Expert Dr. Barry Feinberg in Support of Applied's Motion for Partial Summary Judgment that Surgical Infringes U.S. Patent 5,411,483, Sep. 30, 1999.

Defendant's Memorandum of Points and Authorities in Opposition to Plaintiff's Motions for Partial Summary Judgment of Infringement of U.S. Patents No. 5,407,433 and 5,411,483, Nov. 8, 1999.

Statement of Genuine Issues of United States Surgical Corporation in Opposition to Plaintiff's Motion for Partial Summary Judgment of Infringement of U.S. Patent No. 5,407,433, Nov. 8, 1999.

Statement of Genuine Issues of United States Surgical Corporation in Opposition to Plaintiff's Motion for Partial Summary Judgment of Infringement of U.S. Patent No. 5,411,483, Nov. 8, 1999.

Affidavit of Technical Expert Dr. Anthony Storace, P.E. in Support of United States Surgical Corporation's Opposition to Applied's Motion for Partial Summary Judgment of Infringement of U.S. Patent Nos. 5,407,433 and 5,411,483, Nov. 5, 1999.

Reply Memorandum in Support of Applied's Motion for Partial Summary Judgment that Surgical Infringes U.S. Patent Nos. 5,407,433 and 5,411,483, Nov. 15, 1999.

Order: (1) Denying Plaintiff's Motion for Summary Judgment of Infringement of U.S. Patent No. 5,385,553; (2) Granting Plaintiff's Motions for Partial Summary Judgment of Infringement of U.S. Patent No. 5,407,433, and U.S. Patent No. 5,411,483, Jul. 10, 2000.

Order: Statement of Uncontroverted Facts and Conclusions of Law in Support of Applied's Motion for Partial Summary Judgment that Surgical Infringes U.S. Patent No. 5,407,433, Sep. 30, 1999.

Order: Statement of Uncontroverted Facts and Conclusions of Law in Support of Applied's Motion for Partial Summary Judgment that Surgical Infringes U.S. Patent No. 5,411,483, Jul. 10, 2000.

Defendant United States Surgical Corporation's Memorandum of Points and Authorities in Support of its Motion for Reconsideration, Aug. 4, 2000.

Applied's Opposition to Surgical's Motion for Reconsideration of Court's Jul. 6, 2000 Order; Declaration of Todd G. Friedland, Aug. 14, 2000.

Reply Memorandum in Further Support of Defendant United States Surgical Corporation's Motion for Reconsideration, Aug. 21, 2000.

Defendant's Notice of Motion and Motion for Claim Construction of Loomas Patents, and Memorandum of Points and Authorities in Support thereof, Aug. 25, 2003.

Statement of Uncontroverted Facts and Conclusions of Law in Support of Defendant's Motion for Claim Construction of the Loomas Patents, Aug. 25, 2003.
Affidavit of Technical Expert Dr. Anthony Storace, P.E. in Support of Defendant's Motion for Claim Construction of the Loomas Patents, Aug. 22, 2003.
Declaration of Bradford J. Badke in Support of Defendant's Motion for Claim Construction of the Loomas Patents, Aug. 23, 2003.
Plaintiff Applied's Opposition to Defendant USSC's Motion for Claim Construction of the Loomas Patents, Sep. 17, 2003.
Plaintiff Applied's Statement of Genuine Issues Opposing USSC's Motion for Claim Construction of the Loomas Patents, Sep. 17, 2003.
Declaration of Gregory S. Cordrey in Support of Plaintiff Applied's Opposition to USSC's Motion for Claim Construction of the Loomas Patents, Sep. 17, 2003.
Defendant's Reply Memorandum of Points and Authorities in Further Support of its Motion for Claim Construction of the Loomas Patents, Oct. 2, 2003.
Memorandum of Points and Authorities in Support of Defendant's Motion for Partial Summary Judgment of Invalidity of the Asserted Claims of the Loomas Patents, Feb. 28, 2001.
Statement of Uncontroverted Facts and Conclusions of Law in Support of Defendant's Motion for Partial Summary Judgment of Invalidity of the Asserted Claims of the Loomas Patent, Feb. 28, 2001.
Declaration of Bradford J. Badke in Support of Defendant's Motion for Partial Summary Judgment of Invalidity of the Asserted Claims of the Loomas Patents, Exhibit F, Feb. 27, 2001.
Plaintiffs Opposition to Defendant's Motion for partial Summary Judgment of Invalidity of the Asserted Claims of the Loomas Patents, Mar. 26, 2001.
Applied's Statement of Genuine Issues and Additional Material Facts Opposing USSC's Motion for Partial Summary Judgment of Invalidity of the Asserted Claims of the Loomas Patents, Mar. 26, 2001.
Declaration of Technical Expert Dr. Barry Feinberg in Support of Applied's Opposition to Defendant's Motion for Partial Summary Judgment of Invalidity of the Asserted Claims of the Loomas Patents, Mar. 22, 2001.
Declaration of Bradford J. Badke In Support Of Defendant's Motion For Partial Summary Judgment Of Invalidity Of the Asserted Claims Of the Loomas Patents, Exhibit J, Feb. 27, 2001.
Declaration of Lawrence Cruz in Support of Defendant's Motion for Partial Summary Judgment of Invalidity of the Asserted Claims of the Loomas Patents,.
Defendant's Notice of Motion and Motion for Partial Summary Judgment of Invalidity of the Asserted Claims of the Loomas patents, and Memorandum of Points and Authorities in Support Thereof, Aug. 25, 2003.
Statement of Uncontroverted Facts and Conclusions of Law in Support of Defendant's Motion for Partial Summary Judgment of Invalidity of the Asserted Claims Of the Loomas Patents, Aug. 25, 2003.
Affidavit of Technical Expert Dr. Anthony Storace, P.E. in Support of Defendant's Motion for Partial Summary Judgment of Invalidity of the Asserted Claims of the Loomas Patents, Aug. 22, 2003.
Plaintiff Applied's Opposition to Defendant USSC's Motion for Partial Summary Judgment of Invalidity of the Loomas Patents, Sep. 17, 2003.
Plaintiff Applied's Statement of Genuine Issues and Additional Material Facts Opposing USSC's Motion for Partial Summary Judgment of Invalidity of the Asserted Claims of the Loomas Patents, Sep. 17, 2003.
Declaration of Gregory S. Cordrey in Support of Plaintiff Applied's Opposition to USSC's Motion for Partial Summary Judgment of Invalidity of the Asserted Claims of the Loomas Patents, Exhibit 4, Sep. 17, 2003.
Defendant's Reply Memorandum of Points and Authorities in Further Support of its Motion for Partial Summary Judgment of Invalidity of the Asserted Claims of the Loomas Patents, Oct. 2, 2003.
Memorandum of Points and Authorities in Support of Applied's Motion for Summary Judgment That the Loomas '433 and '483 Patents are not Invalid, Aug. 25, 2003.
Statement of Uncontroverted Facts and Conclusions of Law in Support of Applied's Motion for Summary Judgment That the Loomas '433 and '483 Patents Are Not Invalid, Aug. 25, 2003.
First Declaration of Gregory S. Cordrey in Support of Applied's Motion for Summary Judgment That the Loomas '433 and '483 Patents Are Not Invalid, Exhibit 14, Aug. 25, 2003.
Reply in Support of Applied's Motion for Summary Judgment That the Loomas '433 and '483 Patents Are Not Invalid, Oct. 2, 2003.
Reporter's Transcript of Proceedings, Plaintiffs Motion for Summary Judgment, Nov. 22, 1999.
Reporter's Transcript of Proceedings, Hearing on Defendant's Motion for Summary Judgment of Invalidity of Loomas Patents, Nov. 9, 2001.
Reporter's Transcript of Proceedings, Motions Hearing, Oct. 14, 2003.
Order of the Central District of California in *Applied Medical Resources Corporation* v. *United States Surgical Corporation,* Case No. SACV-99/0625, Oct. 29, 2003.
United States Surgical Corporation's Statement of Genuine Issues in Opposition to Applied's Motion for Summary Judgment That the Loomas 5,407,433 and 5,411,483 Patents Are Not Invalid, Sep. 17, 2003.
Amended Order Invalidating The Loomas Patents, USDC Central District of California, Southern Division Case No. SACV 99/0625 CJC (MLGx), Filed Dec. 23, 2003 in 9 pages.
Declaration of Gregory S. Cordrey vol. 2 in Support of Plaintiff Applied's Opposition to USSC's Motion for Claim Construction of the Loomas Patents with Exhibit 20, p. 2—Exhibit 22, p. 21, USDC Central District of California, Southern Division Case No. SACV 99/0625 CJC (MLGx), Filed Under Seal Pursuant to Protective Order Dated May 19, 2000 and Modified Mar. 2, 2001, Signed Sep. 17, 2003 in 20 pages.
Memorandum of Points and Authorities in Opposition Applied's Motion for Summary Judgment that the Loomas '433 and '483 Patents Are Not Invalid, USDC Central District of California, Southern Division, Case No. SACV 99-625 CJC (MLGx), Filed Under Seal Pursuant to Protective Order Dated May 19, 2000 and Modified Mar. 2, 2001, Signed Sep. 17, 2003 in 30 pages.
Second Declaration of Bradford J. Badke in Support of Defendant's Motion for Summary Judgment of Invalidity of the Asserted Claims of the Loomas Patents with Exhibit N, p. 4—Exhibit T, p. 139, USDC Central District of California, Southern Division, Case No. SACV 99-625 CJC (MLGx), Filed Under Seal, Signed Feb. 27, 2001 in 70 pages.
Second Declaration of Bradford J. Badke in Support of Defendant's Motion for Summary Judgment of Invalidity of the Asserted Claims of the Loomas Patents with Exhibits V, p. 50—Exhibit V, p. 115, USDC Central District of California, Southern Division, Case No. SACV 99-625 CjJC(MLGx), Filed Under Seal, Signed Feb. 27, 2001 in 68 pages.

* cited by examiner

GAS-TIGHT SEAL ACCOMODATING SURGICAL INSTRUMENTS WITH A WIDE RANGE OF DIAMETERS

Matter enclosed in heavy brackets [ ] appears in the original patent but forms no part of this reissue specification; matter printed in italics indicates the additions made by reissue.

FIELD OF THE INVENTION

The invention relates to a gas-tight seal for use in a surgical instrument to provide a gas-tight seal with an instrument passed through the seal. The seal can form a gas-tight seal with instruments having a wide range of diameters.

BACKGROUND OF THE INVENTION

Trocar tubes used in laparoscopic surgery are normally fitted with a gas-tight seal to maintain pneumoperitoneum when a laparoscopic instrument is inserted into the trocar tube. The gas-tight seal is normally built into the rear housing attached to the cannula of the trocar tube, and forms a gas-tight seal with an instrument having an outside diameter that is similar to the internal diameter of the cannula.

In the course of laparoscopic surgery, it is often necessary to insert into the trocar tube a laparoscopic instrument having a diameter that is less than the diameter of the cannula. The gas-tight seal built into the trocar tube cannot provide an adequate gas-tight seal with such a smaller-diameter instrument since known gas-tight seals suffer from an inability to accommodate a wide range of instrument diameters. Known gas-tight seals leak when a smaller-diameter instrument is inserted, and/or impose excessive friction when a larger-diameter instrument is inserted. Known gas-tight seals also have an increased tendency to leak with a smaller-diameter instrument when the instrument is displaced laterally.

In known gas-tight seals, a thin, circular piece of an elastic material is rigidly supported at its periphery. In the center of the elastic material is a circular instrument port through which the instrument passes. The elastic material surrounding the instrument port contacts the instrument, which forms the gas-tight seal. The inability of known gas-tight seals to seal with instruments having a large range of diameters results from this basic construction.

The instrument port must be smaller than the diameter of the instrument so that the instrument can deform the elastic material surrounding the instrument port to form the seal with the instrument. Consequently, when the seal is to accommodate a range of instrument diameters, the instrument port must be smaller than the minimum of the range of instrument diameters for which the seal is designed, so that a minimum-diameter instrument can deform the elastic material. Deforming the elastic material results in a radial force between the elastic material and the instrument. This holds the elastic material in contact with the instrument and maintains the gas-tight seal.

An instrument port diameter that produces the required amount of radial force for a minimum-diameter instrument results in a greater radial force when a larger-diameter instrument is inserted. The greater radial force increases friction between the seal and the instrument. With known gas-tight seals, the maximum of the diameter range, above which friction is so great as to make it impossible to manipulate the instrument, may not be a great deal larger than the minimum of the diameter range, below which the gas-tight seal leaks.

In known gas-tight seals, the radial force between the elastic material and the instrument at the minimum of the diameter range must be increased if the instrument is to be allowed to move laterally in the seal. The increased radial force is required to keep the elastic material remote from the direction of lateral displacement in contact with the instrument, and thus to maintain the gas-tight seal. This increase in the radial force further increases friction between the seal and the larger-diameter instrument, and thus further limits the diameter range that the seal will accommodate.

To enable instruments with a range of diameters to be used in the same trocar tube, and to form a gas-tight seal with instruments having a range of diameters, it is known to fit a trocar tube with an auxiliary gas-tight seal. The auxiliary gas-tight seal supplements the diameter range capability of the main gas-tight seal. For example, the applicant's assignee sells trocar assemblies in which the trocar tube has a 10 mm (0.4") diameter cannula that can accommodate instruments ranging from 5 mm (0.2") and 10 mm (0.4") in diameter. The trocar tube accommodates this range of diameters by providing two auxiliary door-type gas-tight seals in addition to the main gas-tight seal. The main gas-tight seal, which will be described further below, seals with instruments between 9 and 10 mm in diameter; a first auxiliary seal seals with instruments 7 to 8 mm in diameter, and a second auxiliary seal seals with instruments 5 and 6 mm in diameter.

The two auxiliary door-type gas-tight seals are stored on opposite sides of the rear housing of the trocar tube. Each auxiliary seal is mounted in a track that runs up the side and across the rear face of the housing. Before a smaller-diameter instrument is inserted into the cannula, the surgeon must slide the appropriate auxiliary gas-tight seal up the track from the storage position into place on the proximal face of the housing. In this position, the auxiliary seal forms a seal with a lip on the main gas-fight seal, and seals with the smaller-diameter instrument passed through it. If another instrument with a different diameter is later to be inserted into the cannula, the one auxiliary seal must be returned to its storage position, and, if necessary, the other auxiliary seal deployed.

Time is needed in the operating room to move each auxiliary gas seal back and forth from its storage position to its operating position. The process of sliding the auxiliary gas-tight seal can be tedious, especially for gloved hands. The surgeon must remember, or double check, which auxiliary seal is in place before inserting an instrument into the trocar tube. If the auxiliary seal is too large for the instrument, the seal will leak; if the auxiliary seal is too small for the instrument, there will be excessive friction between the seal and the instrument. With an extreme diameter mismatch, the instrument can tear the seal, which would then require that the trocar tube be replaced.

As an example of a different approach to accommodating in a single trocar tube instruments with a range of diameters, U.S. Pat. No. 5,104,383 describes a completely detachable auxiliary seal that allows an instrument as small as 5 mm in diameter to be used in a 10 mm cannula. The auxiliary seal is installed into the rear of the housing before a smaller-diameter instrument is inserted into the cannula. A single auxiliary gas-fight seal is made to accommodate instruments with a range of diameters by including a rigid stabilizer plate to prevent the instrument from being moved laterally relative to the cannula. The stabilizer plate keeps the instrument centered in the cannula, and prevents gas leaks caused by the instrument going off center in the auxiliary seal.

Thus, with known auxiliary gas-tight seals, either a single, wider range, auxiliary gas-tight seal or plural, narrower-range, auxiliary gas-tight seals can be used to accommodate instruments with a range of diameters. If plural, narrower-range, auxiliary gas-tight seals are used, the surgeon has to ensure that the auxiliary gas-tight seal is the appropriate one for the diameter of the instrument being used. If a single, wider-range auxiliary gas-tight seal is used, the surgeon must accept that the range of lateral movement of the instrument in the cannula is limited if the auxiliary gas-tight seal is to seal effectively with an instrument at the minimum of the diameter range.

OBJECTS AND SUMMARY OF THE INVENTION

To overcome the problems of known gas-tight seals, it is an object of the invention to provide a gas-tight seal that accommodates instruments with a wide range of diameters, for example, from 4 to 12 mm.

It is a further object of the invention to provide a gas-tight seal that effectively provides a leak-free seal with an instrument with a diameter at the minimum of the range of diameters.

It is a further object of the invention to provide a gas-tight seal that imposes an acceptably low level of friction on an instrument with a diameter at the maximum of the range of diameters.

It is an object of the invention to provide a gas-tight seal that does not limit the lateral movement of the instrument.

Finally, it is an object of the invention to provide a gas-tight seal that can be built into a trocar tube to allow the trocar tube to accommodate instruments with a wide range of diameters, for example, from 4 to 12 mm.

Accordingly, the invention provides a seal for use in a surgical instrument to provide a gas-tight seal with an instrument passed through the seal. The seal can form a gas-tight seal with an instrument having a diameter within a wide range of diameters. The seal comprises a seal body, an instrument seal, and a laterally-compliant seal mounting device. The seal body includes a bore through which the instrument is passed. The instrument seal is made of an elastic material and is disposed substantially perpendicular to the axis defined by the bore of the seal body. The instrument seal includes an instrument port through which the instrument is passed. The laterally-compliant seal mounting device mounts the instrument seal to the seal body, forms a gas-tight seal between the instrument seal and the seal body, and allows the instrument seal to move freely laterally in response to lateral movement of the instrument.

The instrument seal forms the gas-tight seal with the instrument. The laterally-compliant seal mounting device allows the instrument to move the instrument seal laterally with a relatively small lateral force. This enables a significant reduction to be made in the radial force that the instrument seal is required to exert on the instrument to maintain the gas-tight seal as the instrument is moved laterally. This, in turn, increases the range of instrument diameters that can be used in the seal.

In a preferred embodiment, the laterally-compliant seal mounting device includes a rigid annulus, and a laterally-compliant annulus disposed between the rigid annulus and the seal body. The instrument seal is attached to the rigid annulus with the instrument port inside the annulus.

The laterally-compliant annulus and the instrument seal are preferably provided by an outer radial zone and an inner radial zone, respectively, of a single seal molding. The seal molding additionally includes a rigid annulus anchor radial zone and an anchoring radial zone. The rigid annulus anchor radial zone extends between the inner radial zone and the outer radial zone. The rigid annulus is attached to the rigid annulus anchoring radial zone. The anchoring radial zone extends outwards from the outer radial zone and is attached to the seal body.

A low-friction coating may be applied to the instrument seal to reduce friction between the instrument seal and the instrument. This further increases the range of instrument diameters that can be used with the seal.

The seal may also include a lateral force transmitting device that transmits a lateral force from the instrument directly to the laterally-compliant seal mounting device. The directly-transmitted lateral force moves the instrument seal laterally as the instrument is moved laterally. The lateral force transmitting device preferably transmits the lateral force from the instrument directly to the rigid annulus, and thence to the instrument seal.

The lateral force transmitting device reduces the lateral force between the instrument and the instrument seal required to move the instrument seal laterally. This enables a further reduction to be made in the radial force that the instrument seal must apply to the instrument to maintain a gas-tight seal as the instrument is moved laterally. Reducing the radial force between the instrument seal and the instrument increases the range of instrument diameters that can be used with the seal.

The invention also provides a seal for use in a surgical instrument to provide a gas-tight seal with an instrument passed through the seal. The seal will form a gas-tight seal with an instrument having a diameter within a wide range of diameters. The seal comprises a seal body, a rigid mounting, an instrument seal, and a compliant mounting. The seal body includes a bore through the instrument is passed. The rigid mounting also includes a bore. The instrument seal of made an elastic material and includes an instrument port through which the instrument is passed. The instrument seal is disposed substantially perpendicular to the axis, and is attached to the rigid mounting with the instrument port over the bore of the rigid mounting. The compliant mounting is disposed between the rigid mounting and the seal body.

The instrument seal forms the gas-tight seal with the instrument and is mounted in the rigid mounting. The rigid mounting is, in turn, mounted to the seal body by the compliant mounting. The rigid mounting effectively isolates the instrument seal from the compliant mounting. The compliant mounting allows the instrument to move the instrument seal laterally with a relatively small lateral force. This enables a significant reduction to be made in the radial force that the instrument seal is required to exert on the instrument to maintain the gas-tight seal as the instrument is moved laterally. This, in turn, increases the range of instrument diameters that can be used in the seal.

The seal may also include a low-friction coating applied to the instrument seal, as described above. The seal may also include a lateral force transmitting device that transmits a lateral force from the instrument directly to the rigid mounting, and thence to the instrument seal, substantially as described above.

Finally, the preferred embodiment of the invention provides a seal for use in a surgical instrument to provide a gas-tight seal with an instrument passed through the seal. The seal can form a gas-tight seal with an instrument having a diameter within a wide range of diameters. The seal comprises a seal body, a rigid annulus, and a seal molding. The seal body includes a bore through which the instrument is passed, and a first internal face opposite a second internal face. The internal faces are disposed about the bore. The rigid annulus is slidably mounted between the first internal face and the second internal face. The seal molding is made of an elastic material, and is disposed within the seal body substantially perpendicular to the axis. The seal molding includes an inner zone providing an instrument seal and including an instrument port through which the instrument is passed. The seal molding also includes a corrugated, laterally compliant, outer zone, and a rigid annulus anchor zone extending between the inner zone and the outer zone. The rigid annulus is attached to the rigid annulus anchor zone. Finally, the seal molding includes an anchoring zone extending outwards from the outer zone. The anchoring zone is attached to the seal body.

The inner zone of the seal molding forms the gas-tight seal with the instrument and is mounted in the rigid annulus. The rigid annulus is, in turn, mounted to the seal body by the compliant outer part of the seal molding. The rigid annulus effectively isolates the instrument seal part of the seal molding from the compliant outer zone of the seal molding, and also interacts with the internal faces of the seal body to restrict axial movement of the instrument seal. The compliant outer zone of the seal molding allows the instrument to move the inner zone of the seal molding laterally with a relatively small lateral force. This enables a significant reduction to be made in the radial force that the inner zone of the seal molding is required to exert on the instrument to maintain the gas-tight seal as the instrument is moved laterally. This, in turn, increases the range of instrument diameters that can be used in the seal.

The seal may also include a low-friction coating applied to the seal molding, as described above. The seal may also include a lateral force transmitting device that transmits a lateral force from the instrument directly to the rigid annulus, and thence to the instrument seal, as described above.

DETAILED DESCRIPTION OF THE INVENTION

Figure 1:
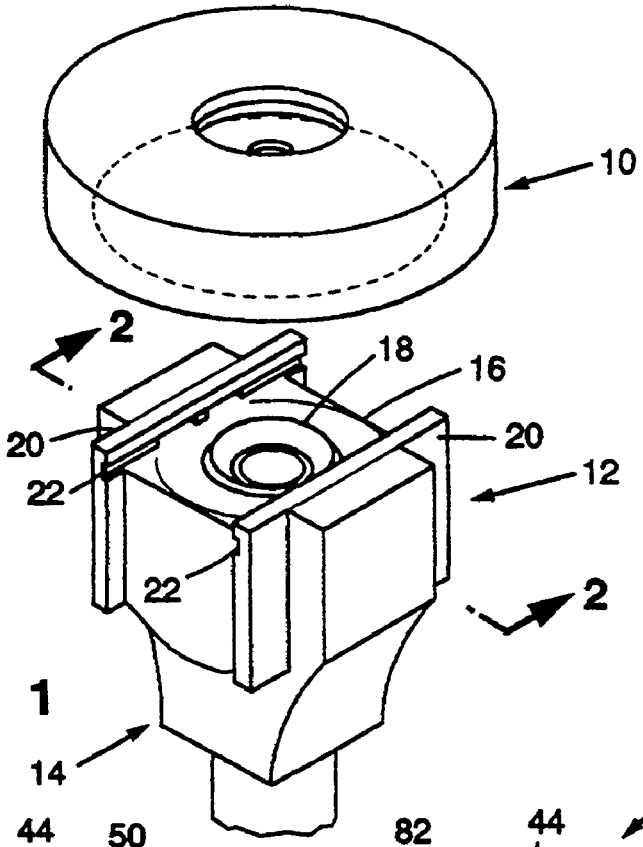
FIG. 1 is a perspective view of an auxiliary gas-tight seal according to the invention aligned with the rear housing of a trocar tube, prior to attaching the auxiliary gas-tight seal to the rear housing.

The conventional gas-tight trocar tube seal, described above, uses the same piece of elastic material to form the gas-tight seal with the instrument, and to accommodate lateral displacement of the instrument. The need to accommodate lateral displacement of the instrument requires that, to prevent the seal from leaking, the radial force between the elastic material and the instrument be increased for an instrument at the minimum of the range of diameters. This reduces the maximum of the range of diameters above which there is excessive friction between the elastic material and the instrument.

The gas-tight seal according to the invention uses different structures to provide the gas-tight seal with the instrument and to accommodate lateral displacement of the instrument. This enables the radial force between the gas-tight seal and the instrument to be reduced for an instrument at the minimum of the range of diameters. This, in turn, reduces friction between the seal and a larger-diameter instrument, and thus increases the maximum of the range of diameters.

Additionally, in the gas-tight seal according to the invention, at least the part of the seal that contacts the instrument is preferably dry-lubricated. This provides a further reduction in friction between the seal and the instrument, and further increases the maximum of the range of diameters. Accordingly, the gas-tight seal according to the invention presently provides a gas-tight seal with instruments having a greater than 3:1 range of diameters, and maintains the gas-tight seal when an instrument in the diameter range is laterally displaced. The present preferred embodiment provides a gas-tight seal with instruments ranging in diameter from 4 mm to 12 mm (0.16" to 0.48").

The preferred embodiment of the gas-tight seal according to the invention will next be described. The preferred embodiment is an auxiliary gas-tight seal that is intended to be attached to the rear housing of a trocar tube after the trocar assembly has been used to puncture the body wall, and the trocar has been withdrawn from the trocar tube.

The preferred embodiment is an auxiliary gas-tight seal because the self-shielding mechanism of the trocar of the trocar assembly sold by the applicant's assignee operates by snapping the trocar distally into the cannula after the trocar tip has penetrated the body wall. In this trocar assembly, the trocar passes through a large-diameter, conventional gas-tight seal. If the gas-tight seal according to the invention were substituted for the conventional large-diameter gas-tight seal, friction between the gas-tight seal according to the invention and the trocar would be sufficiently high to impede the operation of the self-shielding mechanism. Friction in the gas-tight seal according to the invention is higher than in the large-diameter conventional gas-tight seal because the considerably smaller diameter instrument port in the gas-tight seal according to the invention. Nevertheless, friction in the gas-tight seal according to the invention is significantly reduced compared with a conventional gas-tight seal having the same diameter instrument port.

The gas-tight seal according to the invention is not limited to use as an auxiliary gas-tight seal, however. A seal according to the invention could be built into, and form the main gas-tight seal in, a trocar tube for use in a trocar assembly in which the self-shielding mechanism does not move the trocar rapidly through the seal. Such a trocar is shown, for example, in U.S. Pat. No. 4,601,710.

FIG. 1 shows a perspective view of the auxiliary gas-tight seal 10 according to the invention aligned with the rear housing 12 of the trocar tube 14, just prior to attaching the auxiliary gas-tight seal to the rear housing. The rear face 16 of the rear housing 12 includes the main gas-tight seal 18 in its center. On opposite sides of rear face are the side walls 20 in which are formed the grooves 22. The rear housing includes the side walls 20 and the grooves 22 as part of the mounting for the two door-type auxiliary gas-tight seals (not shown) formerly fitted to the rear housing, as described above. The auxiliary gas-tight seal 10 includes lugs that engage in the grooves 22 to retain the auxiliary trocar seal in position on the rear face 16 of the rear housing 12. This way of attaching the auxiliary gas-tight seal 10 allows the auxiliary gas-tight seal 10 to replace the conventional door-type auxiliary gas-tight seals formerly fitted without the need to change the tooling used to mold the rear housing 12.

Figure 2:
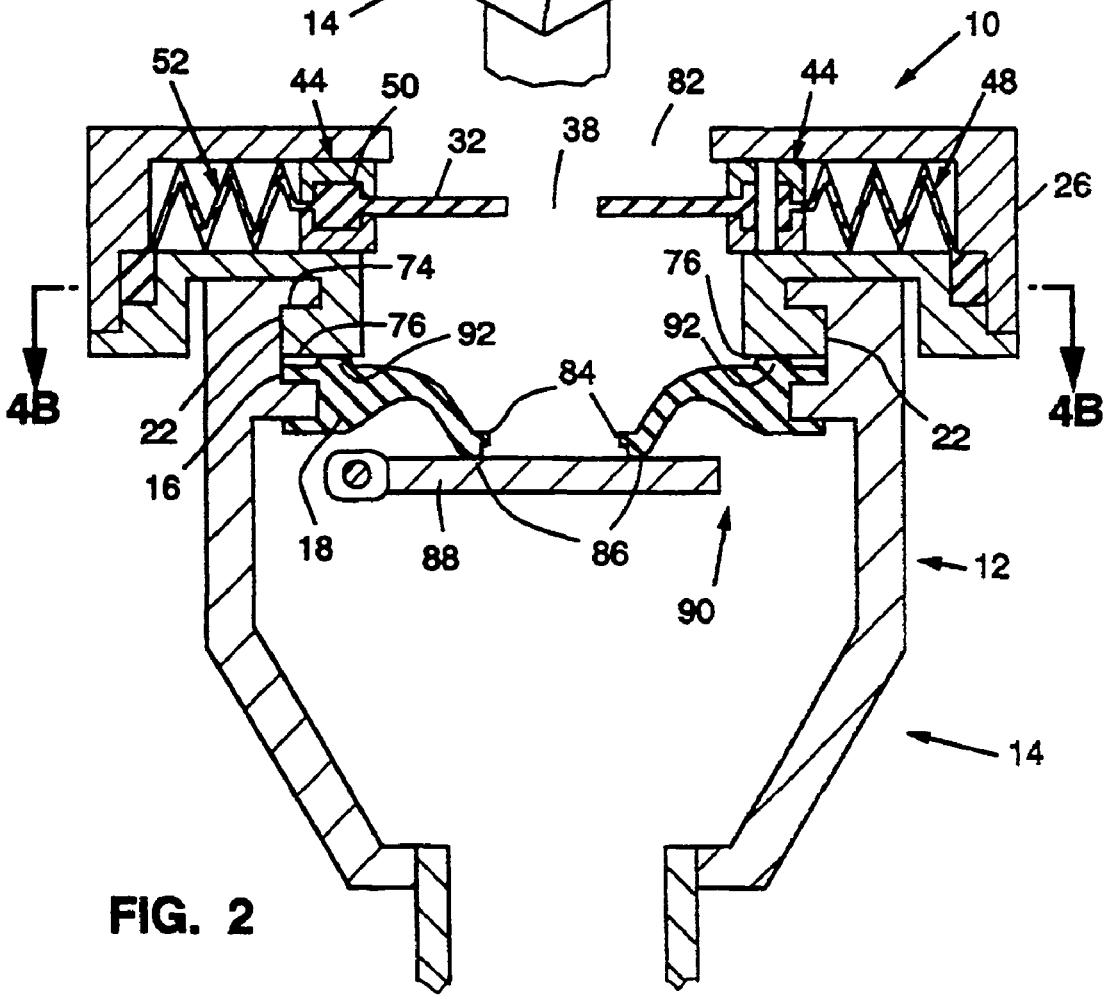
FIG. 2 is a cross sectional view of the auxiliary gas-tight seal according to the invention attached to the rear housing of a trocar tube.

A cross section of the auxiliary gas-tight seal 10 attached to the rear housing 12 is shown in FIG. 2. The auxiliary gas-tight seal 10 is shown in perspective and in cross section in FIGS. 3A and 3B, respectively. The auxiliary gas-tight seal 10 will now be described in detail with reference to these figures.

The auxiliary gas-tight seal 10 includes three main components: the seal body 30 which attaches to the rear housing 12, the instrument seal 32, and the seal mounting 34 for the instrument seal 32. The instrument seal is a piece of a elastic material in which the instrument port 38 is formed, preferably in its center. The instrument seal 32 forms the gas-tight seal with an instrument passed through the instrument port 38. The instrument seal 32 is mounted in the seal mounting 34 to form the laterally-compliant seal 40.

The seal mounting 34 is laterally compliant to allow the instrument seal 32 to move laterally in response to lateral movement of the instrument passed through the instrument port 38. The seal mounting 34 is preferably also axially stiff, to hold the instrument seal 32 in position axially when an instrument is inserted into or withdrawn from the instrument port. The seal mounting 34 includes the anchoring ring 42 and the stabilizing ring 44. The stabilizing ring includes the stabilizing ring halves 44A and 44B, and the locking pins 46.

The preferred embodiment includes the seal molding 48, a part of which provides the instrument seal 32, and the rest of which provides part of the seal mounting 34. The seal molding 48 includes four distinct, radially separated zones, the instrument seal 32, the stabilizing ring anchor 50, the corrugated zone 52, and the anchoring ring 42. The seal molding 48 is made of an elastic material, preferably silicone rubber, but it can alternatively be molded from other suitable elastic materials, such as latex.

The instrument seal 32 and the seal mounting 34 could alternatively be separate components joined at the stabilizing ring 44. This alternative construction is more complex, but enables different materials to be used for the instrument seal 32 and the seal mounting 34. For example, the seal mounting 34 could be made from an inelastic material, such as Mylar™ film.

The part of the seal molding 48 providing the instrument seal 32 forms a gas-tight seal with an instrument (not shown) passed through the instrument port 38 in the center of the seal molding. Compared with the part of the seal molding 48 forming the corrugated zone 52, the part forming the instrument seal 32 is relatively thick, about 1 mm (0.04") in the preferred embodiment. This enables this part of the seal molding to exert sufficient radial force against the instrument to form a gas-tight seal, even with an instrument at the minimum of the range of diameters. The part of the seal molding forming the instrument seal 32 is also relatively thick to prevent it from being tom when a hook-shaped instrument is withdrawn from the instrument port.

The present embodiment accommodates instruments having a range of diameters, i.e., the instrument seal 32 forms a gas-tight seal with an instrument of a minimum diameter, and provides an acceptably low level of friction with an instrument as large as the maximum diameter. The minimum instrument diameter that can be accommodated depends on the diameter of the instrument port 38. In the present preferred embodiment, the instrument port 38 is 3 mm (0.12") in diameter. With an instrument port of this diameter, the instrument seal 32 forms a gas-tight seal with an instrument as small as 4 mm (0.16") in diameter. The preferred embodiment can be adapted to accommodate different ranges of instrument diameters by changing the diameter of the instrument port 38. For example, a 2.2 mm (0.09") diameter instrument port will provide a gas-tight seal with a 3 mm (0.12") diameter instrument.

When a larger-diameter instrument is inserted through the instrument port 38, the instrument stretches the elastomeric material of the seal molding 48 forming the instrument seal 32. This causes the part of the seal molding providing the instrument seal 32 to exert a radial force against the instrument, which results in friction between the instrument seal 32 and the instrument. To reduce this friction, the seal molding 48 is preferably coated with a dry lubricant. Reducing friction increases the maximum of the range of instrument diameters that the auxiliary gas-tight seal 10 can accommodate without excessive friction between the instrument and the instrument seal.

The preferred dry lubricant is poly-p-xylxylene, a crystalline organic solid, a thin film of which is low vacuum deposited from the vapor phase onto the seal molding 48. Poly-p-xylxylene is sold under the brand name Parylene C by Union Carbide. An alternative anti-friction coating is titanium, vapor deposited onto the surface of the seal molding 48. It is only necessary to deposit the dry lubricant coating on the part of the seal molding 48 forming the instrument seal 32, but it is simpler to deposit the coating on all the seal molding. Other suitable surface modification techniques or anti-friction coatings can also be used. With the dry lubricant coating, an instrument having a diameter as large as three times the minimum diameter can be inserted into the instrument port 38 in the seal molding 48 without excessive friction. Thus, in the present preferred embodiment, an instrument as large as 12 mm (0.48") in diameter can be inserted into the 3 mm diameter instrument port without excessive friction. It is envisaged that the present embodiment can be developed to accommodate a range of instrument diameters greater than the present 3:1.

The seal mounting 34 for the instrument seal 32 comprises the stabilizing ring 44; and the stabilizing ring anchor 50, the corrugated zone 52, and the anchoring ring 42, all of which form part of the seal molding 48. The part of the seal molding 48 forming the anchoring ring 42 is considerably thicker than the part of the seal molding forming the instrument seal 32. The anchoring ring 42 is relatively rigid, and serves to locate the laterally-compliant seal 40 in the seal body 30. The anchoring ring is located in an annular groove formed by the inner annular step 58 in the base 60 and the annular step 64 in the cap 66. The face 54 and the face 56 of the anchoring ring contact the inner annular step 58 in the base 60, and the face 62 of the anchoring ring contacts the annular step 64 in the cap 66. When the cap and the base are mated to form the seal body 30, the anchoring ring is slightly compressed between the annular step 64 and the inner annular step 58. This forms a gas-tight seal between the anchoring ring and the seal body.

The part of the seal molding 48 forming the stabilizing ring anchor 50 is located between the instrument seal 32 and the corrugated zone 52. The stabilizing ring anchor 50 is an annular region in which the thickness of the seal molding 48 is increased on both sides. The stabilizing ring anchor serves to locate the seal molding 48 laterally with respect to the stabilizing ring 44.

The corrugated zone 52 interconnects the stabilizing ring anchor 50 and the anchoring ring 42. The part of the seal molding 48 forming the corrugated zone 52 is between one tenth and one half of the thickness of the part of the seal molding forming the instrument seal 32. In the preferred embodiment, the part of the seal molding forming the corrugated zone is about 0.2 mm (0.008") thick, and is also corrugated, as shown. The thinness of the corrugated zone 52 and its corrugated structure provide lateral compliance between the inner periphery, (i.e., the stabilizing ring 44) and the outer periphery (i.e., the anchoring ring 42) of the corrugated zone. The amount of radial force that must be applied to the stabilizing ring to displace laterally the stabilizing ring and the part of the corrugated zone to which it is attached is relatively small. Thus, the lateral force that an instrument passed through, the instrument port 38 must apply to the instrument seal 32 to displace laterally the instrument seal 32, the stabilizing ring 44, and the part of the corrugated zone to which the stabilizing ring is attached is relatively small. Consequently, the additional radial force that the instrument seal 32 must apply to an instrument having a diameter at the minimum of the range of diameters to maintain the gas-tight seal with the instrument as the instrument is displaced laterally is also relatively small. Reducing the additional radial force reduces the radial force that the instrument seal 32 exerts when a larger-diameter instrument is inserted into the instrument port 38. This, in turn, reduces friction between the seal and the instrument and increases the range of instrument diameters that the seal can accommodate.

The stabilizing ring 44 interconnects the instrument seal 32 and the corrugated zone 52, and transmits any radial force applied to the instrument seal 32 uniformly to the corrugated zone 52. The stabilizing ring 44 also preferably transmits axial forces resulting from inserting and withdrawing an instrument into and from the instrument port 38 directly to the seal body 30, i.e., to the base 60 when an instrument is inserted, and to the cap 66 when an instrument is withdrawn. The stabilizing ring, by isolating axial forces from the corrugated zone 52, and by transmitting radial forces uniformly to the corrugated zone, enables the strength of the corrugated zone to be minimized, and the lateral compliance of the corrugated zone to be maximized.

The stabilizing ring 44 comprises the stabilizing ring halves 44A and 44B, and the pins 46. The stabilizing ring halves are annulus-shaped moldings of a suitable low-friction plastic, such as ABS, polycarbonate, or PTFE. Each stabilizing ring half includes in one face the annular groove 68 that mates with the stabilizing ring anchor 50 in the seal molding 48. The stabilizing ring halves 44A and 44B are held in place on opposite sides of the seal molding 48 by the plural pins 46 inserted through one of the stabilizing ring halves (e.g., the stabilizing ring half 44A), the stabilizing ring anchor 50, and the other of the stabilizing ring halves (e.g., the stabilizing ring half 44B). The pins 46 pass through the stabilizing ring anchor 50, where the material of the seal molding 48 is thicker, and forms a gas-tight seal with each pin 30. This prevents the pins 46 from providing a gas leakage path.

The behavior of the laterally-compliant seal 40 when an instrument passed through the instrument port is laterally displaced will now be contrasted with the behavior of the conventional gas-tight seal. In the conventional gas-tight seal, the elastic material surrounding the instrument port is rigidly mounted at its periphery. The elastic material surrounding the instrument port stretches to accommodate lateral displacement of the instrument. Sufficient excess radial force must be provided between the elastic material and the instrument to keep the elastic material remote from the direction of the lateral displacement in contact with the instrument and therefore preserve the gas-tight seal.

In the laterally-compliant seal 40 in the auxiliary gas-tight seal 10 according to the invention, the elastic material surrounding the instrument port 38 is also rigidly mounted at its periphery, but the rigidly-mounted elastic material is, in turn, compliantly mounted. When the instrument passing through the instrument port is displaced laterally, the seal mounting 34 allows the whole of the instrument seal 32 to move laterally. This is illustrated in FIG. 3C, in which the center line 41 of the instrument (not shown) is displaced laterally to the point indicated by the line 43. The lateral movement of the instrument seal is accommodated by the corrugated zone 52, the thin, corrugated material of which makes it laterally compliant. The force between the instrument and the instrument port, and hence the amount of stretching of the elastic material surrounding the instrument port, required to displace the instrument seal laterally is small. Thus, compared with a conventional seal, the laterally-compliant seal 40 requires that considerably less excess radial force be provided between the instrument seal and the instrument to maintain contact with instrument when the instrument is laterally displaced. This, in turn, reduces the amount of friction between the instrument seal and the instrument when a larger-diameter instrument is inserted into the instrument port, and allows the seal to accommodate a larger range of instrument diameters.

Figure 3A:
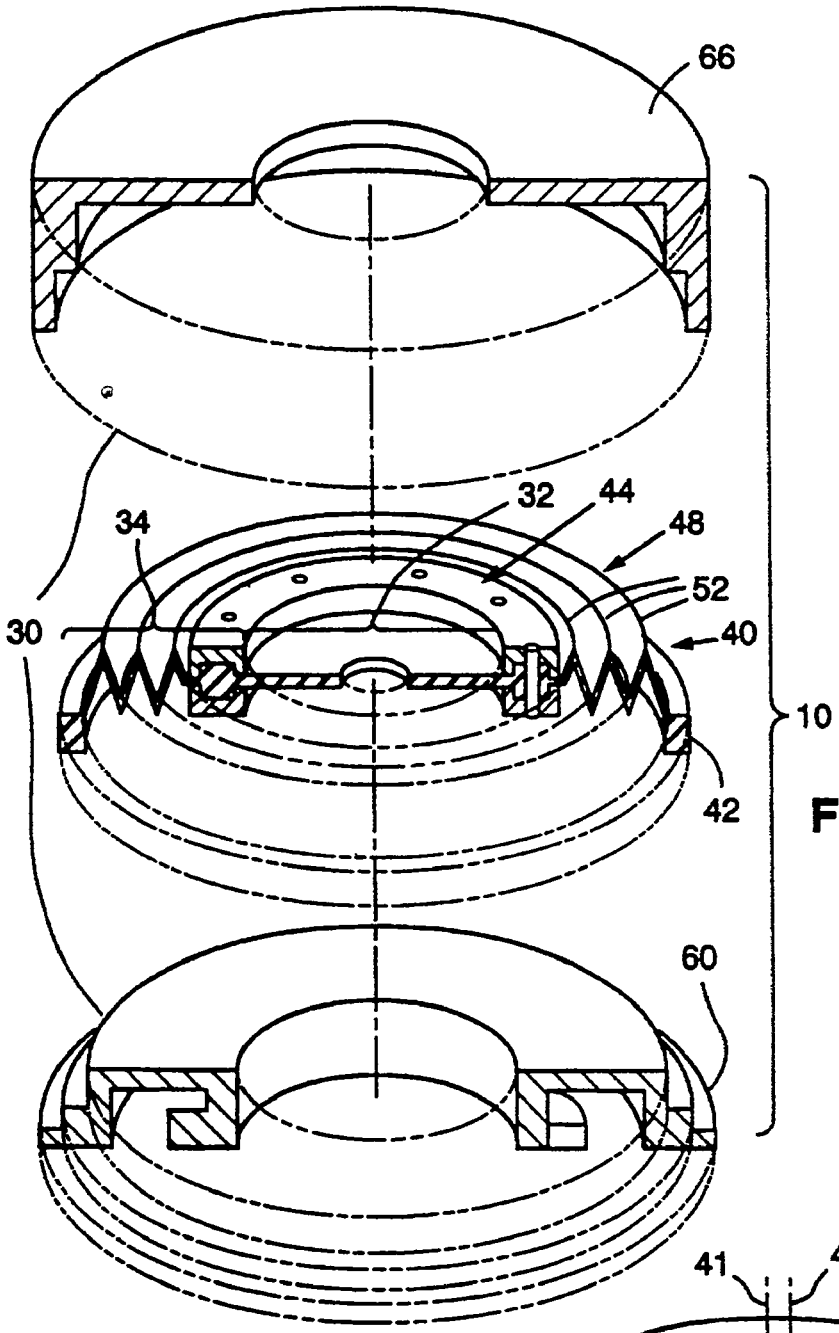
FIG. 3A is an exploded perspective view of an auxiliary gas-tight seal according to the invention showing its three main components.
Figure 3C:
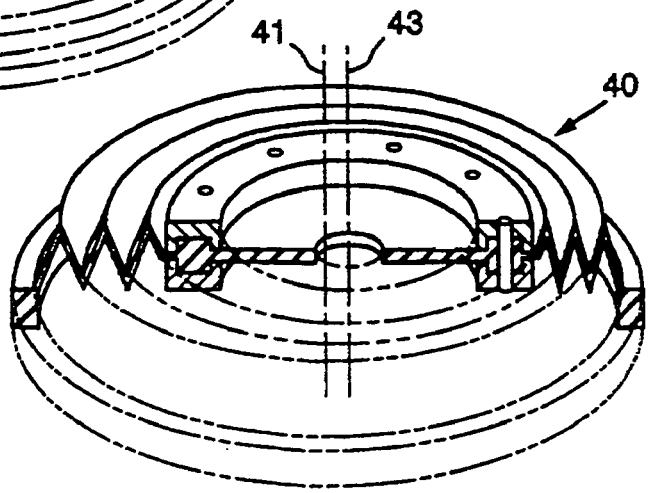
FIG. 3C is a perspective view of the laterally-compliant seal of the auxiliary gas-tight seal according to the invention showing how laterally displacing an instrument inserted into the instrument port laterally displaces the instrument seal and the stabilizing ring.

The seal body 30 includes the base 60 and the cap 66, as shown in FIG. 3A. The base 60 is a molding of a suitable plastic, such as ABS, or polycarbonate. The base includes the internal face 70 over which the stabilizing ring 44 of the seal mounting 34 can slide laterally. The base also includes the inner annular step 58 and the outer annular step 80. The inner annular step 58, together with the annular step 64 in the cap, locates the anchoring ring 42 of the seal molding 48, as described above. The outer annular step 80 abuts the edge 81 of the cap 60, which defines the axial location of the cap 66 relative to the base 60. This, in turn, defines the amount of compression applied to the anchoring ring 42 when the cap and the base are mated to form the seal body 30. This also defines the clearance between the internal face 70 of the base 60 and the internal face 78 of the cap 66, and hence the clearance between the stabilizing ring 44 and the internal faces 70 and 78.

The base also includes the bore 72, which has a diameter of slightly greater than the diameter as the largest-diameter instrument that can be accommodated by the main gas-tight seal in the trocar tube, plus twice the thickness of the instrument seal 32. Surrounding the bore 72 are the lugs 74 and the plane sealing surface 76 with which the auxiliary gas-tight seal 10 is attached to the rear face 16 of the rear housing 12 (FIG. 1). The lugs 74 are preferably tapered.

The lugs 74 and the plane sealing surface 76 are specific to the preferred way of attaching the auxiliary gas-tight seal 10 to the rear housing of the trocar tube sold by the applicant's assignee. The auxiliary gas-tight seal 10 could be attached to the rear housing of the trocar tube made by the applicant's assignee in other ways, which would require a different arrangement of the base 60 and/or the cap 66. Moreover, the auxiliary gas-tight seal 10 could be adapted for attaching to the rear housings of trocar tubes made by others, which might also require a different arrangement of the base 60 and/or the cap 66. Finally, a gas-tight seal similar to the auxiliary gas-tight seal 10 can be built into the rear housing of a trocar tube, in which case, the base 60 would be formed as part of the rear housing molding.

The cap 66 is also a molding of a suitable plastic such as ABS or polycarbonate. The cap fits over the base 60, and includes the internal face 78, with respect to which the stabilizing ring 44 of the seal mounting 34 can slide laterally. The cap 66 also includes the inner annular step 64 and the edge 81. The annular step 64 clamps the anchoring ring 42 of the seal molding 48 into the annular step 58 in the base 60, as described above. The edge 81 defines the relative axial location of the base and the cap, as described above.

The cap 66 also includes the central bore 82, which also has a diameter of slightly greater than the diameter as the largest-diameter instrument that can be accommodated by the main gas-light seal in the trocar tube, plus twice the thickness of the instrument seal 32.

The cap 66 is attached to the base 60 by a suitable snap arrangement, a suitable adhesive, by ultrasonic welding, or by some other suitable method. The cap may be adapted for attaching the auxiliary gas-tight seal 10 to the rear housing of the trocar tube in addition to, or as an alternative to, the attachment arrangements on the base 60 already described.

Figure 3B:
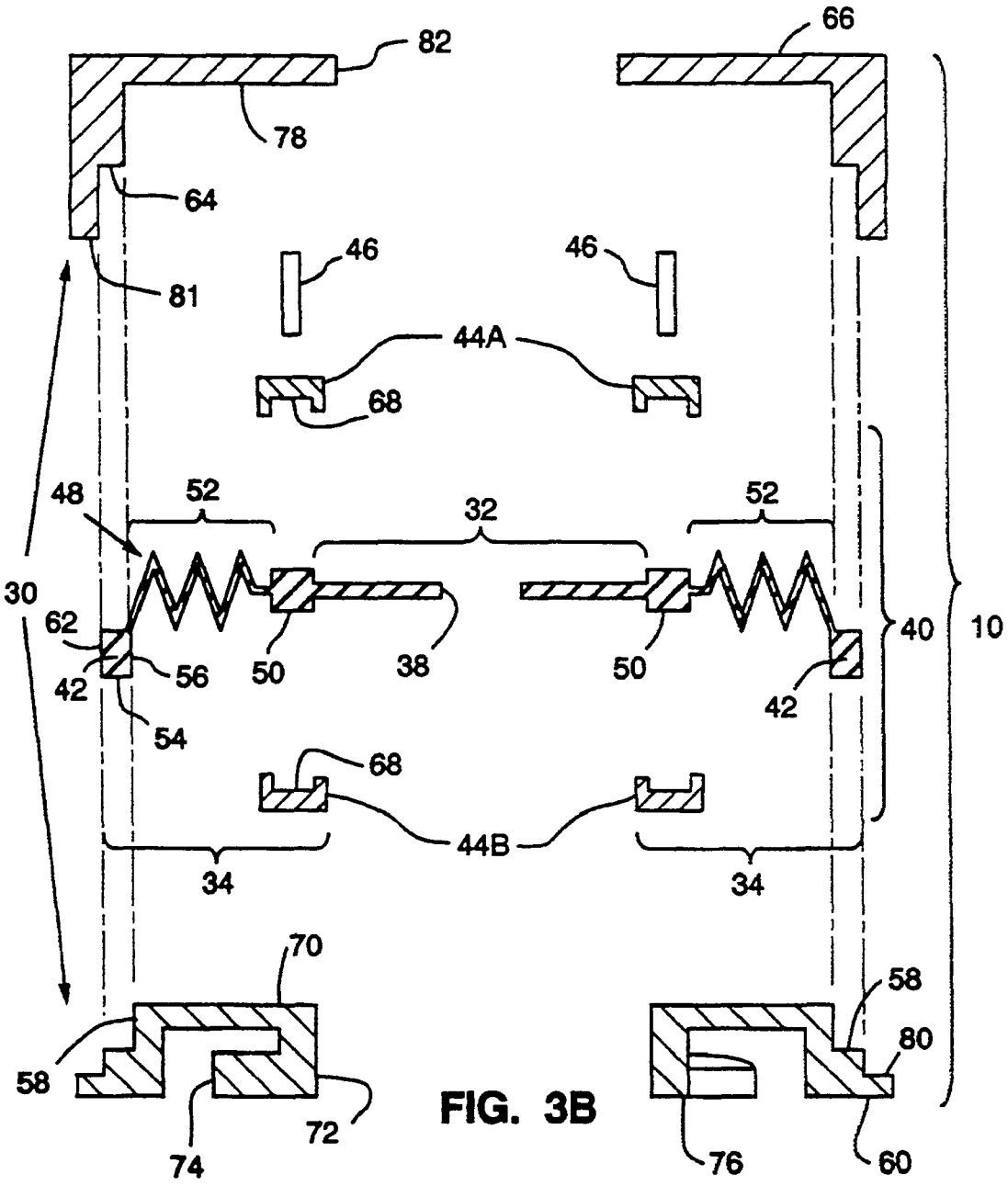
FIG. 3B is an exploded cross-sectional view of auxiliary gas-tight seal according to the invention.
Figure 3D:
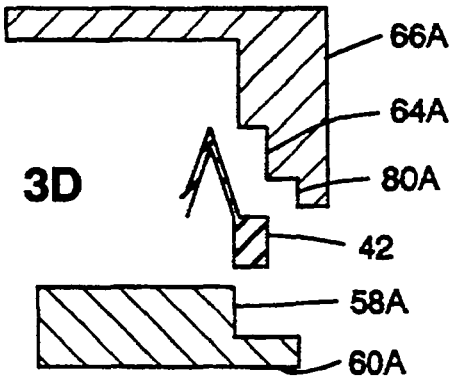
FIG. 3D is a cross-sectional view of pan of an alternative embodiment of the cap and the base of an auxiliary gas-tight seal according to the invention.

As an alternative to the arrangement shown, the cap 66A may be formed with two annular steps, and the base 60A may be formed with a single annular step, as shown in FIG. 3D. The cap 66A is formed with an inner annular step 64A and an outer annular step 80A, and the base is formed with the wide annular step 58A. The annular groove formed between the inner annular step 64A in the cap 66A and the inner part of the wide annular step 58A in the base locates and seals with the anchoring ring 42. The outer part of the wide annular step 58A in the base 60A abutting the outer annular step 80A in the cap MA defines the relative axial location of the base and the cap.

The arrangement for attaching the auxiliary gas-tight seal 10 to the rear housing 12 of the trocar tube made by the applicant's assignee will now be described with reference to FIG. 2. FIG. 2 shows a cross sectional view of the auxiliary gas-tight seal 10 in place on the rear face 16 of the housing 12 of the trocar tube 14.

In the rear housing 12, the main gas-tight seal 18 is an elastomeric molding that engages with the rear face 16 as shown. The main gas-tight seal includes the main sealing lip 84, which seals with the trocar (not shown) or other instrument passed through the main gas-tight seal. The main gas-tight seal also includes the annular inner sealing lip 86, which forms a gas-tight seal with the spring-loaded door 88. The spring-loaded door 88 swings in the direction indicated by the arrow 90 to form a seal with the inner sealing lip 86 when no instrument is inserted into the main gas-tight seal 18.

The main gas-tight seal 18 also includes the annular outer sealing lip 92, which is provided to form a gas-tight seal with the door-type auxiliary gas-tight seal formerly included in the rear housing, as described above. When the auxiliary gas-tight seal 10 is attached to the trocar tube 11 sold by the applicant's assignee, the outer sealing lip 92 forms a gas-tight seal with the plane sealing surface 76 of the base 60 of the auxiliary gas-tight seal 10, as shown. The plane sealing surface 76 is kept in contact with the outer sealing lip 92 by the lugs 74 engaging in the grooves 22 in the rear housing 12.

Figure 4A:
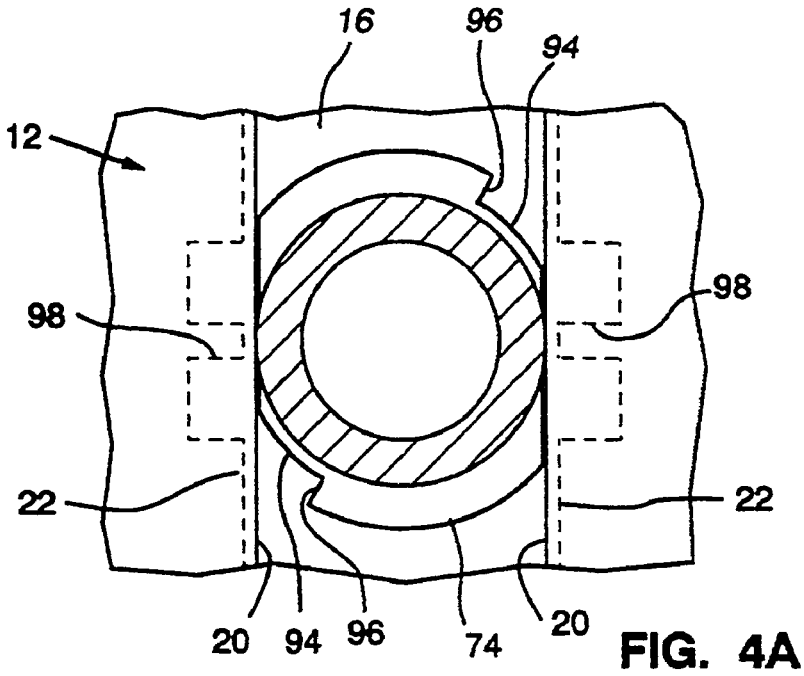
FIG. 4A is a cross-sectional view of the lower part of the base of the auxiliary gas-tight seal according to the invention and the rear housing of a trocar tube prior to engaging the lugs on the base with grooves in the rear housing.
Figure 4B:
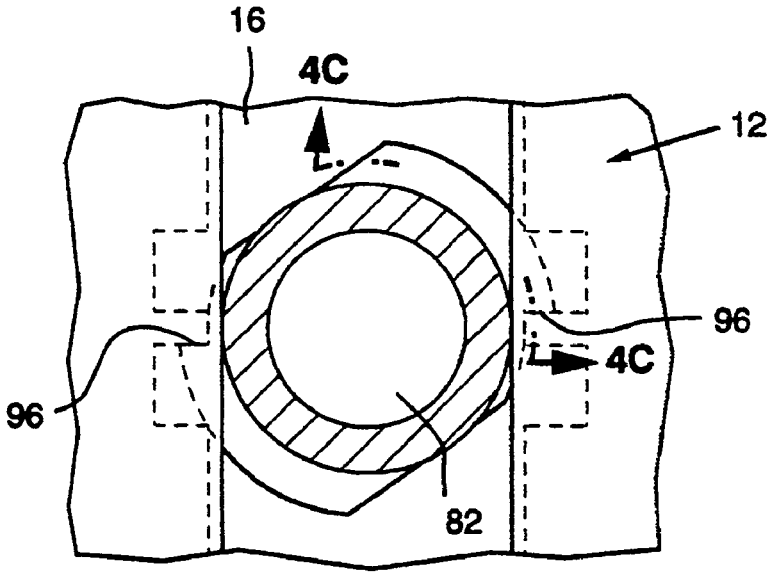
FIG. 4B is a cross-sectional view of the lower part of the base of the auxiliary gas-tight seal according to the invention and the rear housing of a trocar tube prior to engaging the lugs on the base with grooves in the rear housing.
Figure 4C:
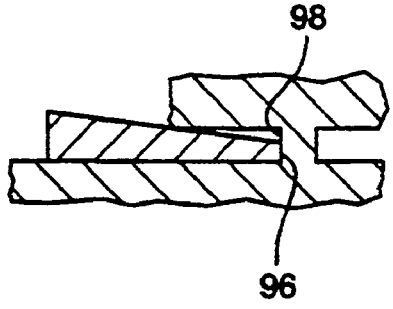
FIG. 4C is a cross-sectional view of the one of the lugs on the base of the auxiliary gas-tight seal according to the invention engaged with one of the grooves in the rear housing of the trocar tube. The drawing shows how the lug is tapered.

FIGS. 4A and 4B show a cross section of the rear housing 12 and part of the base adjacent to the lugs 74 before and after engaging the lugs in the grooves 22. Each lug includes a cut-away part 94, which enables the lugs to fit between the walls 20. To attach the auxiliary gas-tight seal 10 to the rear housing 12, the surgeon grasps the rear housing in one hand, holds the auxiliary gas-tight seal in the other, and presents the auxiliary gas-tight seal to the rear housing such that the cut-away part 94 of each lug is inserted between the walls 20, as shown in FIG. 4A. The surgeon then rotates the auxiliary gas-tight seal in a clockwise direction, looking from the top, to engage the lugs 74 into the grooves 22. The lugs 74 are tapered, as shown in FIG. 4C, such that, as the auxiliary gas-tight seal is rotated, the tapered lugs engaging with the grooves 22 moves the plane sealing face 76 into engagement with the outer sealing lip 92 (see FIG. 2). The surgeon stops rotating the auxiliary gas-tight seal when the stop 96 on each lug is fully engaged with the corresponding stop 98 in the grooves 22. Juxtaposing the stop 96 with the stop 98 and the lugs 74 with the grooves 22 positively locates the auxiliary gas-tight seal 10 in all three dimensions relative to the rear housing 12.

The surgeon can then insert an instrument having any diameter in the specified range of diameters accommodated by the gas-tight seal into the bore 82, and then through the instrument port 38. The surgeon can move a smaller-diameter instrument laterally to the extent defined by the bore 82, if desired.

The surgeon can remove the auxiliary gas-tight seal 10 at any time simply by removing the instrument from the auxiliary gas-tight seal, rotating the auxiliary gas-tight seal 10 counter-clockwise until the lugs 74 disengage from the grooves 22, and withdrawing the auxiliary gas-tight seal from the rear housing 12.

The shape of the auxiliary gas-tight seal 10 and the simple attachment mechanism makes it easy to attach the auxiliary gas-tight seal to, and to remove the auxiliary gas-tight seal from, the rear housing 12 of the trocar tube 14, even with gloved hands. However, it is envisaged that, in practice, because the preferred embodiment of the auxiliary gas-tight seal can accommodate instruments having a 3:1 range of diameters, for example, from 4 mm to 12 mm, the auxiliary gas-tight seal will be fitted to the trocar tube immediately after the trocar has been removed frown the trocar tube, and will remain attached to the trocar tube throughout the rest of the procedure. Only if the trocar were reinserted into the trocar tube, or if some other unprotected sharp instrument were inserted into the trocar tube, would the auxiliary gas-tight seal have to be removed to prevent the trocar or sharp instrument from cutting the instrument seal 32.

Figure 5:
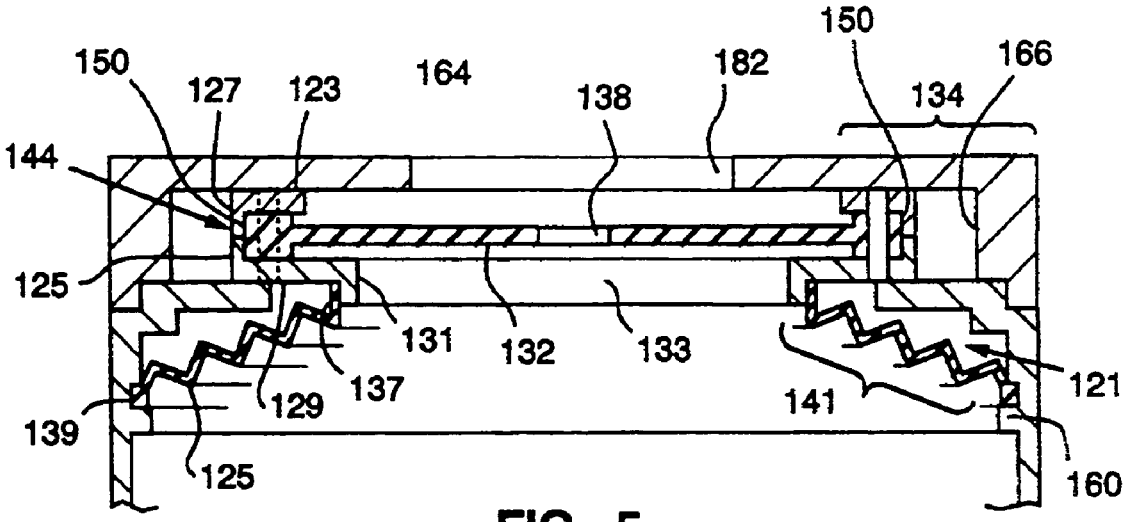
FIG. 5 is a cross-sectional view of a first alternative embodiment of an auxiliary gas-tight seal according to the invention.

An alternative embodiment of the auxiliary gas-tight seal according to the invention is shown in FIG. 5. In this embodiment, parts that are similar to those in the preferred embodiment shown in FIGS. 3A and 3B are numbered with the same reference numbers with 100 added. In the alternative embodiment shown in FIG. 5, a different configuration of the seal mounting is used; the instrument seal 132 and the seal mounting 134 are provided using separate components; and the shapes of the cap 166 and the base 160 constituting the seal body 130 are changed.

The instrument seal 132 is similar to the instrument seal 32 shown in FIGS. 3A and 3B, and is molded of an elastic material, such as silicone rubber, with the stabilizing ring anchor 150 as its outer periphery. The instrument seal includes the instrument port 138.

The seal mounting 134 includes the stabilizing ring 144, the stabilizing ring anchor 150, and the corrugated seal 121. The stabilizing ring 144 includes the stabilizing ring halves 123 and 125, which mate with the stabilizing ring anchor 150. The stabilizing ring half 123 is similar to the stabilizing ring halves 44A and 44B shown in FIGS. 3A and 3B, but its outer curved face 127 is changed because there is no seal molding to pass through it. The stabilizing ring half 125 is substantially changed relative to the stabilizing ring half 44B. The plane face 129 of the stabilizing ring half 125 is extended radially inwards toward the instrument port 138, and then is extended axially away from the instrument seal 132 to form the lip 131. The lip 131 defines the periphery of a bore 133 which has a diameter about 50% greater than the diameter of the bore 164 in the cap 166.

The corrugated seal 121 is a molding of an elastic material, for example, silicone rubber. The corrugated seal includes an inner anchoring ring 137 and an outer anchoring ring 139 interconnected by a corrugated section 141. The anchoring rings are preferably thicker than the corrugated section.

The inner anchoring ring 137 is adapted for attaching to the lip 133 by means of a suitable adhesive, a metal or plastic clamp (not shown), or some other suitable means. The outer anchoring ring 139 is adapted for attaching to the base 160 by means of a suitable adhesive, a metal or plastic clamp (not shown), or some other suitable means. Alternatively, the outer anchoring ring can be compressed in an annular groove (not shown) formed between a step on the base 160 and a corresponding step on a suitable annular sleeve (not shown) fitting inside the base similar to the way in which the base fits inside the cap in FIGS. 3A and 3B.

The alternative embodiment shown in FIG. 5 operates similarly to the preferred embodiment described with reference to FIGS. 3A and 3B. The instrument seal 132 is free to move laterally between the cap 166 and the base 160. This allows the excess radial force between the instrument seal 132 and the instrument to be reduced, which, in turn, reduces friction between the instrument seal 132 and an instrument having a diameter at the maximum of the range of diameters. Thus, the seal can accommodate a greater range of instrument diameters without leaking and without excessive friction.

The stabilizing ring 144 isolates the instrument seal 132 from the seal mounting 134, as before, and also transfers axial forces directly from the instrument seal 132 to the seal body 130, comprising the cap 166 and the base 160.

The seal mounting 134 is laterally compliant while providing a gas-tight seal between the seal body 130 and the instrument seal 132. To move the instrument seal 132 laterally requires that the instrument exert relatively little radial force on the instrument port 138.

Figure 6:
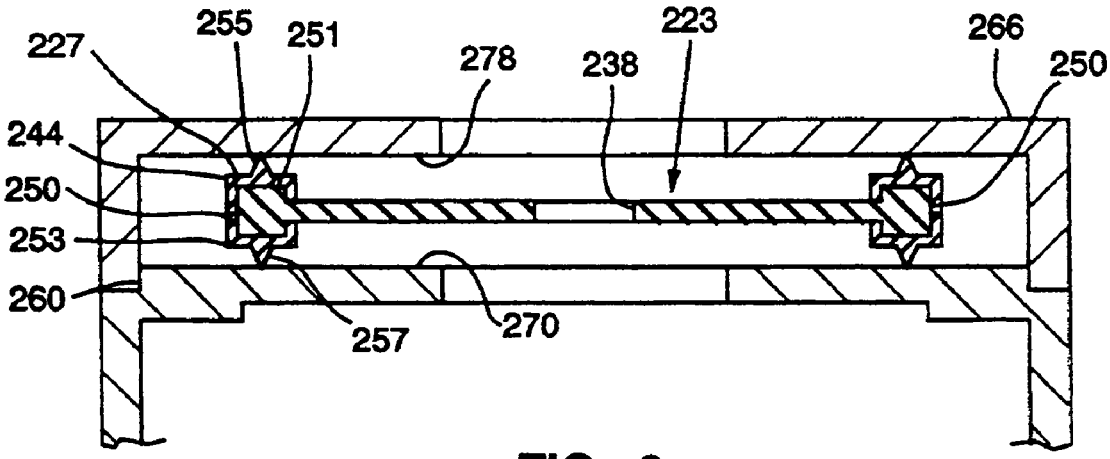
FIG. 6 is a cross-sectional view of a second alternative embodiment of an auxiliary gas-tight seal according to the invention.

In a further alternative embodiment, shown in FIG. 6, the corrugated seal 141 shown in FIG. 5, and the planar corrugated seal 52 shown in FIGS. 3A and 3B are dispensed with, and the laterally-compliant seal is provided by a sliding seal between the stabilizing ring and the seal body.

In FIG. 6, parts that are similar to the embodiments shown in FIGS. 3A and 3B, and FIG. 5 are numbered with the same reference numbers with 100 or 200, respectively, added. The base 260 and the cap 266 are similar to the base 60 and the cap 66 shown in FIGS. 3A and 3B, except that no provision is made for mounting the anchoring ring 42 (FIGS. 3A and 3B). The instrument seal 232 is similar to the instrument seal 132 shown in FIG. 5. As in FIG. 5, the instrument seal 232 is molded with the stabilizing ring anchor 250 at its periphery.

The stabilizing ring anchor 250 mates with the stabilizing ring halves 251 and 253, respectively. Both stabilizing ring halves 251 and 253 are similar to the stabilizing ring half 123 shown in FIG. 5, but the plane face of each stabilizing ring half is modified to include the projecting annular wiper 255 and 257, respectively. Alternatively, a groove can be formed in the flat surface of each stabilizing ring half, and an annular wiper of a different material can be affixed into the groove.

The wiper 255 contacts internal face 278 of the cap 266. The wiper 257 contacts the internal face 270 of the base 260. Contact between the wiper 257 and the internal face 270 forms a primary sliding gas-tight seal. Contact between the upper wiper 255 and the internal face 278 forms a secondary gas-tight seal that seals any gas that escapes past the primary sliding gas-tight seal.

The axially-opposed primary and secondary gas-tight seals require a relatively small axial force between the wipers and their respective internal faces to provide an effective gas-tight seal. This seal remains gas-tight when an axial load is imposed on the seal, such as that imposed when an instrument is inserted or withdrawn, despite the small force between the wipers and their respective sealing faces. It is desirable to have a relatively small force between the wipers and their respective sealing surfaces to minimize friction, and thus maximize the lateral compliance of the instrument seal 232. Friction can be further reduced by coating the wipers 255 and 257 and the internal faces 270 and 278 with a suitable anti-friction layer.

Withdrawing an instrument from the instrument port 238 tends to move the stabilizing ring 244 away from the base 260, which tends to break the primary gas-tight seal. However, in moving away from the base 260, the stabilizing ring 244 moves towards the cap 266. This increases the contact force between the wiper 255 and the internal face 270, and strengthens the secondary gas-tight seal. On the other hand, inserting an instrument into the instrument port tends to move the stabilizing ring 244 towards the base 260, which strengthens the primary gas-tight seal.

Figure 7:
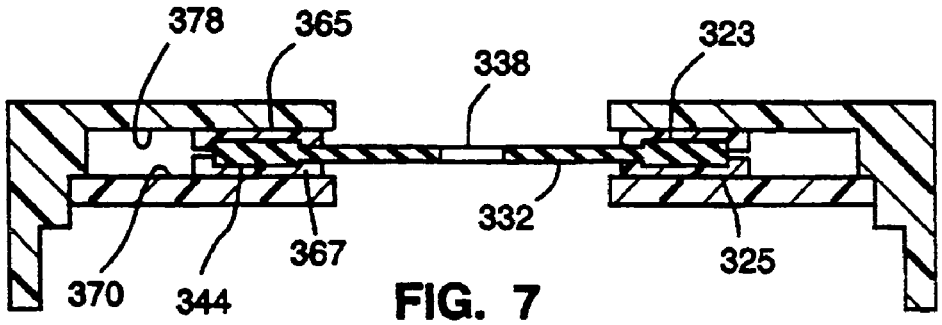
FIG. 7 is a cross-sectional view of a third alternative embodiment of an auxiliary gas-tight seal according to the invention.

FIG. 7 shows a simplified version of the arrangement shown in FIG. 6 in which the wipers are omitted from the stabilizing ring 344. Parts similar to parts shown in FIG. 6 are numbered with the same reference numbers with 100 added. In this embodiment, the internal faces 370 and 378, the mating surfaces of the cap 366 and the base 360, and the plane surfaces of the stabilizing ring 344 are formed with sufficient precision that the gap between the plane faces of the stabilizing ring and the respective internal faces of the cap and the base is of the order of 25 μm (0.001"). This dimension is large enough to allow the stabilizing ring to slide freely between the cap and the base. Gas pressure acting on the instrument seal 332 moves the plane surface 365 of the stabilizing ring half 323 into contact with the internal face 378. This forms a gas-tight seal between the plane surface 365 and the internal face 378. Inserting an instrument into the instrument port 338 may break this seal, but forces the plane face 367 of the stabilizing ring half 326 into contact with the internal face 370. This forms a gas-tight seal between the plane surface 367 and the internal face 370.

The radial force between the instrument seal 32 (FIG. 3A) and the instrument can be further reduced by transmitting directly from the instrument to the stabilizing ring the lateral force required to move the seal mounting 34 laterally. This relieves the instrument seal of the task of transmitting this lateral force, which enables the radial force between the instrument seal and a minimum-diameter instrument to be further reduced. Reducing the radial force between the instrument seal and a minimum-diameter instrument increases the range of instrument diameters that the seal can accommodate.

A number of arrangements which include a lateral force transmitting mechanism to transmit directly from the instrument to the stabilizing ring 44 the force required to move the seal mounting laterally will now be described. FIGS. 8A-8C, 9A, 9B, 10, 11A and 11B only show the stabilizing ring 444 and the instrument seal 432. The lateral force transmitting mechanism embodiments shown in these Figures and in FIGS. 12A and 12B may be applied to any of the main embodiments shown in FIGS. 3A and 3B, 5, 6, and 7, all of which include a stabilizing ring and an instrument seal.

Figure 8A:
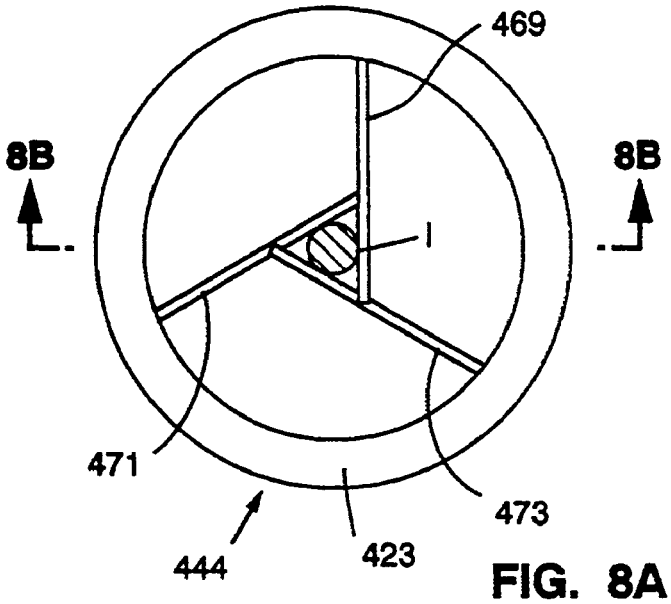
FIG. 8A is a plan view of the stabilizing ring and instrument seal of an auxiliary gas-fight seal according to the invention including a first embodiment of a lateral force transmitting mechanism according to the invention.
Figure 8B:
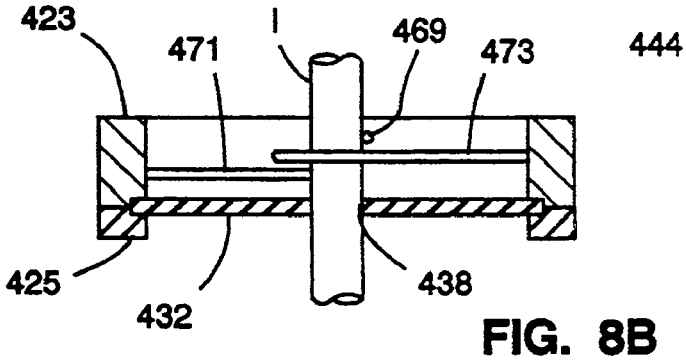
FIG. 8B is a cross-sectional view of the stabilizing ring and instrument seal of the auxiliary gas-tight seal according to the invention including the first embodiment of the lateral force transmitting mechanism according to the invention.
Figure 8C:
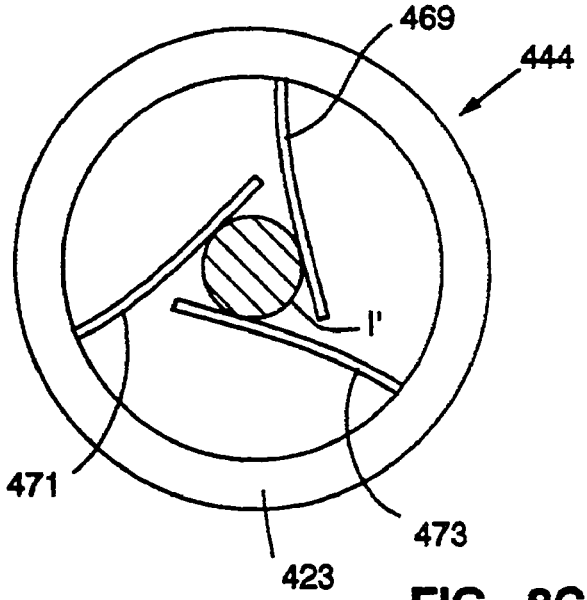
FIG. 8C is a plan view of the stabilizing ring and instrument seal of the auxiliary gas-tight seal according to the invention including the first embodiment of the lateral force transmitting mechanism according to the invention with a larger-diameter instrument inserted.

In the simple embodiment of the lateral force transmitting mechanism shown in FIGS. 8A through 8C, the thickness of one of the stabilizing ring halves comprising the stabilizing ring 444 is increased to accommodate the lateral force transmitting mechanism. In the simple lateral force transmitting mechanism, the increase in the thickness of the stabilizing ring half 423 is relatively small because the simple lateral force transmitting mechanism has a relatively low profile. The more complex lateral force transmitting mechanisms shown in FIGS. 9A and 9B, 10, and 11A and 11B require a greater increase in the thickness of the stabilizing ring half 423.

In the simple lateral force transmitting mechanism shown in FIGS. 8A through 8C, three wire springs 469, 471, and 473 are attached in a radially-symmetrical arrangement to the stabilizing ring half 423. The wire springs are radially offset so that they are substantially tangential to the instrument port 438. The parts of the wire springs adjacent to the instrument port 438 may overlap one another as shown. This may be achieved by appropriately bending each wire spring, or by mounting each wire spring at a different point in the thickness of the stabilizing ring, as shown in FIG. 8B.

With the lateral force transmitting mechanism shown, the wire springs 469, 471, and 473 are biased into contact the instrument, such as the instrument I, inserted into the instrument port 438. The wire springs exert a radial compressive force against the instrument. The compressive force is as radially symmetrical as is possible with a radial force applied by three discrete elements. The compressive force can be made more symmetrical at the expense of greater complexity by increasing the number of wire springs.

When the instrument I is moved laterally, the instrument applies a lateral force to one or more of the wire springs 469, 471, and 473. Each wire spring to which the lateral force is applied transmits the lateral force directly to the stabilizing ring 444. The lateral force thus applied directly to the stabilizing ring moves the stabilizing ring and the instrument seal 432 laterally with the lateral movement of the instrument. In this way, the lateral force transmitting mechanism moves the instrument seal laterally and considerably reduces the force between the instrument seal and the instrument required to move the instrument seal laterally.

The elasticity of the wire springs 469, 471, and 473 enables the wire springs to move radially when a larger-diameter instrument, such as the instrument I' shown in FIG. 8C, is inserted into the instrument port.

Like the instrument seal 432, the wire springs 469, 471, and 473 exert a radial force against the instrument. This radial force increases with increasing diameter of the instrument. However, friction on the instrument resulting from the radial force exerted by the wire springs is less than that resulting from the radial force exerted by the instrument seal because the coefficient of friction between the wire springs and the instrument is less than that between the instrument seal and the instrument.

Figure 9A:
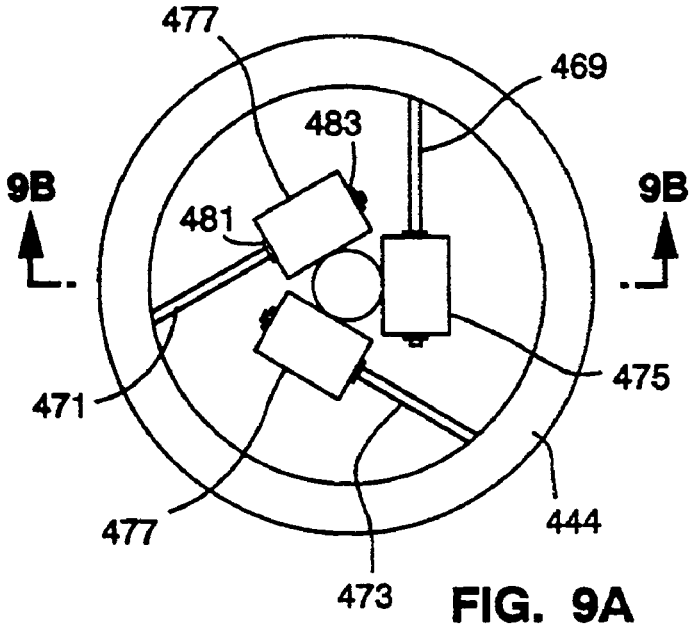
FIG. 9A is a plan view of the stabilizing ring and instrument seal of an auxiliary gas-tight seal according to the invention including a second embodiment of the lateral force transmitting mechanism according to the invention.
Figure 9B:
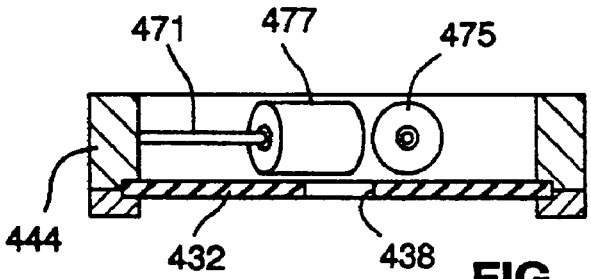
FIG. 9B is a cross-sectional view of the stabilizing ring and instrument seal of the auxiliary gas-tight seal according to the invention including the second embodiment of the lateral force transmitting mechanism according to the invention.

The parts of the wire springs 469, 471, and 473 remote from the stabilizing ring 444 may be fitted with suitably-shaped paddles to make inserting the instrument easier. Inserting the instrument may be made even easier by fitting each wire spring with a roller, as shown in FIGS. 9A and 9B. Each of the wire springs 469, 471, and 473 is fitted with a roller 475, 477, and 479, respectively. Each roller is free to rotate on its respective wire spring, and is axially located on the wire spring by bushes, or some other suitable device. The bushes 481 and 483 are shown retaining the roller 477 on the wire spring 471, for example.

Figure 10:
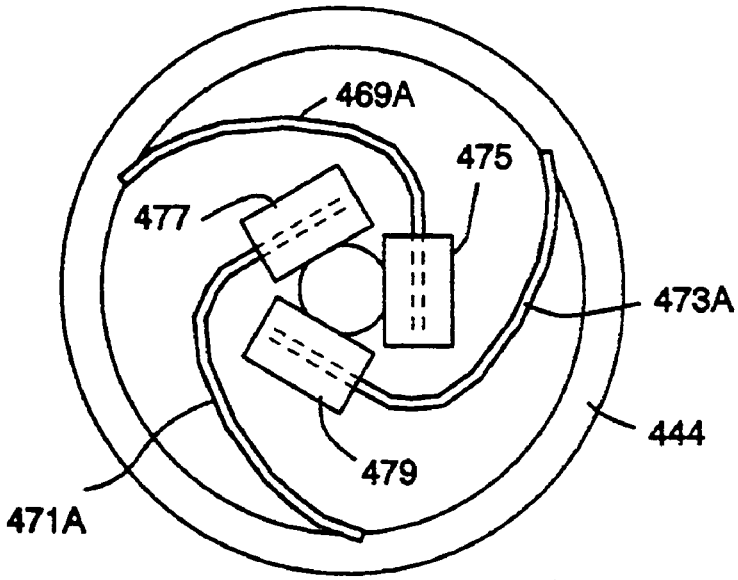
FIG. 10 is a plan view of the stabilizing ring and instrument seal of an auxiliary gas-tight seal according to the invention including a third embodiment of the lateral force transmitting mechanism according to the invention.

The radial force applied to the instrument by the lateral force transmitting mechanism can be made less dependent on the instrument diameter increases by making the wire springs longer, as shown in FIG. 10. In FIG. 10, the wire springs 469A, 471A, and 473A are curved, which enables their length to be increased within the confines of the stabilizing ring 444. In this embodiment, the rollers 475, 477, and 479 can be omitted, or can be replaced by paddles, if desired.

Figure 11A:
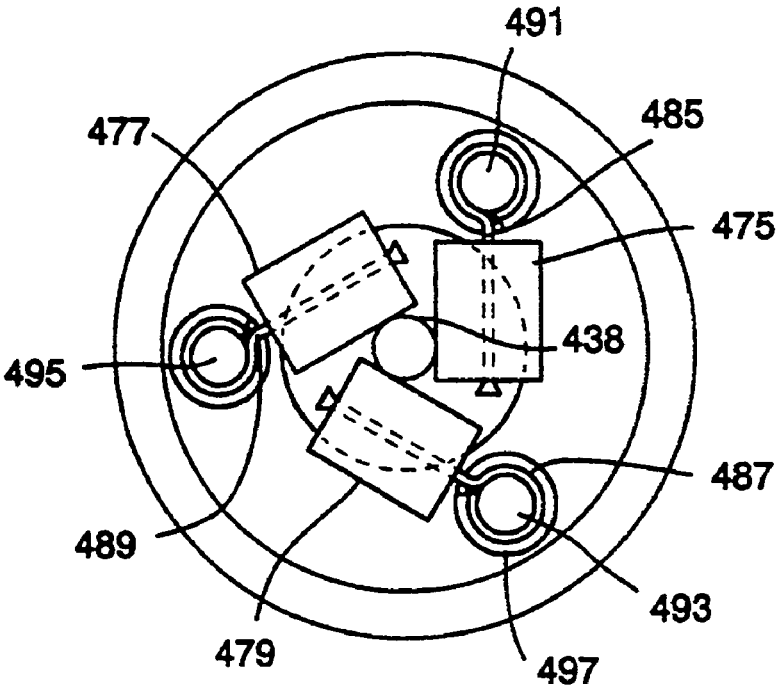
FIG. 11A is a plan view of the stabilizing ring and instrument seal of an auxiliary gas-tight seal according to the invention including a fourth embodiment of the lateral force transmitting mechanism according to the invention.
Figure 11B:
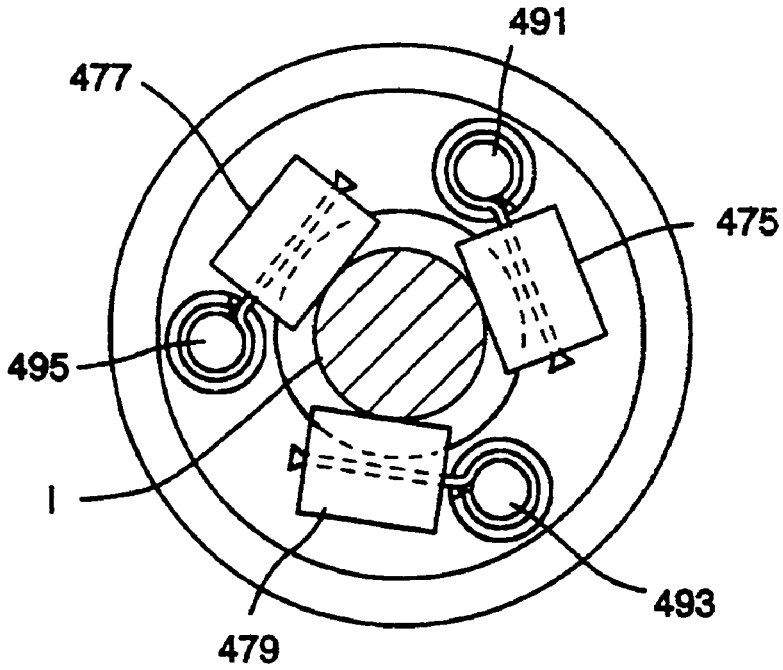
FIG. 11B is a plan view of the stabilizing ring and instrument seal of the auxiliary gas-tight seal according to the invention including the fourth embodiment of the lateral force transmitting mechanism according to the invention with a larger-diameter instrument inserted into the instrument port.

In the embodiment shown in FIGS. 11A and 11B, the rollers 475, 477, and 479 are mounted on the axles 485, 487, and 490, respectively. The axles 485, 487, and 489 swivel on the pins 491, 493, and 495 mounted on the stabilizing ring 444. A hairspring arrangement 495 biases each pivoted axle towards the instrument port 438. Such an arrangement makes the radial force applied to the instrument by the lateral force transmitting mechanism less dependent on the instrument diameter. When an instrument, such as the instrument I, is inserted into the instrument port 438, the rollers are forced outwards, as shown in FIG. 11B, but the long effective length of the hairspring arrangement makes the radial force between the rollers and the instrument relatively independent of the diameter of the instrument.

Figure 12A:
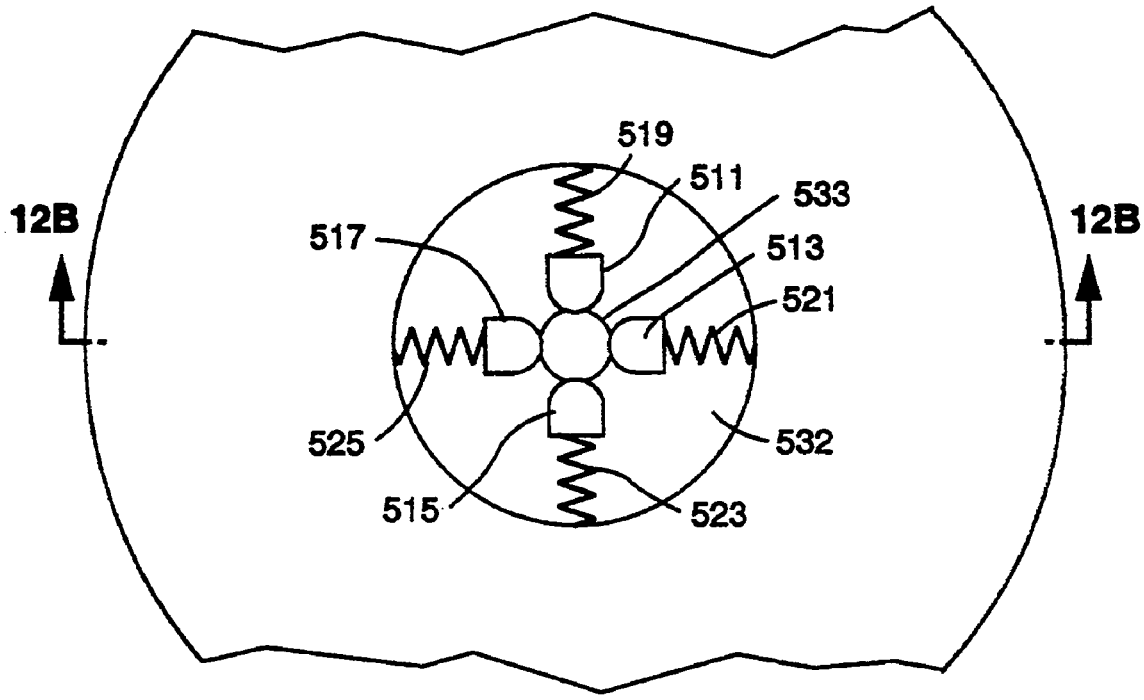
FIG. 12A is a plan view of an auxiliary gas-tight seal according to the invention including a fifth embodiment of a lateral force transmitting mechanism according to the invention.
Figure 12B:
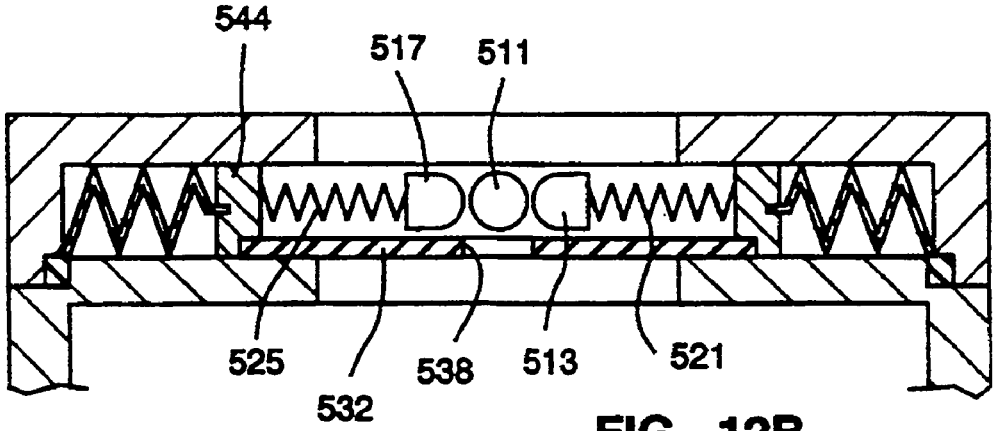
FIG. 12B is a cross-sectional view of the auxiliary gas-tight seal according to the invention including the fifth embodiment of the lateral force transmitting mechanism according to the invention.

FIGS. 12A and 12B show an arrangement of spring-loaded bumpers. Each of the four bumpers 511, 513, 515, and 517 is mounted on a compression spring 519, 521,523, and 525 inside the stabilizing ring 544. This arrangement exerts a radial compressive force against an instrument inserted into the instrument port 538. When the instrument is moved laterally, the bumpers and springs transmit a lateral force directly to the stabilizing ring 544. This moves the instrument seal 532 laterally, and considerably reduces the force between the instrument seal and the instrument required to move the instrument seal laterally.

Although illustrative embodiments of the invention have been described herein in detail, it is to be understood that the invention is not limited to the precise embodiments described, and that various modifications may be practiced within the scope of the invention defined by the appended claims.

I claim:

1. Apparatus for use in a surgical instrument to provide a gas-tight seal with an instrument passed through the seal, the instrument having a diameter in a wide range of diameters, the apparatus comprising:

a seal body including a bore wherethrough the instrument is passed, the bore defining an axis; and an instrument seal assembly, including:

a rigid annulus, and an instrument seal of an elastic material, the instrument seal: including an instrument port wherethrough the instrument is passed; and being attached to the rigid annulus with the instrument port inside the annulus, the instrument seal assembly being mounted in the seal body in a manner restricting axial movement and permitting free lateral movement of the instrument seal assembly in response to movement of the instrument passed through the instrument port, *wherein no provision is made for anchoring a portion of the instrument seal assembly to the seal body*.

2. The apparatus of claim 1, wherein:

the seal body includes a first internal face opposite a second internal face, the internal faces being disposed about the bore; and the rigid annulus is slidably mounted between the first internal face and the second internal face.

3. The apparatus of claim 2, wherein the seal body comprises:

a cap including the first internal face and a curved side having an annular step formed therein; and a base including the second internal face, the base fitting into the cap and engaging with the annular step to define a spacing between the rigid annulus and the internal faces of the seal body.

4. The apparatus of claim 2, wherein the seal body comprises:

a cap including the first internal face and a curved side having an edge: and a base including the second internal face and an annular step, the base fitting into the cap such that the edge of the cap engages with the annular step to define a spacing between the rigid annulus and the internal faces of the seal body.

5. The apparatus of claim 2, additionally comprising a lateral force transmitting means for transmitting a lateral force from the instrument directly to the [laterally-compliant seal mounting means] *instrument seal assembly* to move the instrument seal laterally with a reduced lateral force between the instrument and the instrument port.

6. The apparatus of claim 2, additionally comprising a low-friction coating applied to the instrument seal.

7. The apparatus of claim 2, wherein the rigid annulus includes *a* first plane face opposite a second plane face, and *the rigid annulus* is mounted in the seal body with the first plane face opposite the first internal face of the seal body and the second plane face opposite the second internal face of the seal body.

8. The apparatus of claim 7, wherein the [laterally-compliant seal mounting means] *instrument seal assembly* additionally includes:

a first annular wiper attached to the first plane face of the rigid annulus and contacting the first internal face of the seal body; and a second annular wiper attached to the second plane face of the rigid annulus and contacting the second internal face of the seal body.

9. The apparatus of claim 8, wherein the seal body comprises:

a cap including the first internal face and a curved side having an annular step formed therein: and a base including the second internal face, the base fitting into the cap and engaging with the annular step to define a spacing between the rigid annulus and the plane faces of the seal body.

10. The apparatus of claim 8, wherein the seal body comprises:

a cap including the first internal face and a curved side having an edge; and a base including the second internal face and having an annular step formed therein, the base fitting into the cap such that the edge engages with the annular step to define a spacing between the rigid annulus and the plane faces of the seal body.

11. The apparatus of claim 8, additionally comprising a lateral force transmitting means for transmitting a lateral force from the instrument directly to the [laterally-compliant seal mounting means] *rigid annulus* to move the instrument seal laterally with a reduced lateral force between the instrument and the instrument port.

12. The apparatus of claim 8, additionally comprising a low-friction coating applied to the instrument seal.

[13. The apparatus of claim 1, wherein the instrument seal assembly additionally includes a laterally-compliant annulus disposed between the rigid annulus and the seal body.]

[14. The apparatus of claim 13, wherein:

the seal body includes a first internal face opposite a second internal face, the internal faces being disposed about the bore; and the rigid annulus is slidably mounted between the first internal face and the second internal face.]

[15. The apparatus of claim 14, wherein the seal body comprises:

a cap including the first internal face and a curved side having an annular step formed therein: and a base including the second internal face, the base fitting into the cap and engaging with the annular step to define a spacing between the rigid annulus and the internal faces of the seal body.]

[16. The apparatus of claim 14, wherein the seal body comprises:

a cap including the first internal face and a curved side having an edge; and a base including the second internal face, and having an annular step formed therein, the base fitting into the cap such that the edge engages with the annular step to define a spacing between the rigid annulus and the internal faces of the seal body.]

[17. The apparatus of claim 13, additionally comprising a lateral force transmitting means for transmitting a lateral force from the instrument directly to the laterally-compliant seal mounting means to move the instrument seal laterally with a reduced lateral force between the instrument and the instrument port.]

[18. The apparatus of claim 13, additionally comprising a low-friction coating applied to the instrument seal.]

[19. The apparatus of claim 13, wherein the laterally-compliant annulus is corrugated and is disposed between the rigid annulus and a part of the seal body axially displaced from the rigid annulus and the instrument seal.]

[20. The apparatus of claim 19, wherein:

the seal body includes a first internal face opposite a second internal face, the internal faces being disposed about the bore; and the rigid annulus is slidably mounted between the first internal face and the second internal face.]

[21. The apparatus of claim 20, wherein:

the seal body includes a part that extends axially from the second internal face in a direction remote from the first internal face;

the second plane face of the rigid annulus includes a part that extends radially inwards relative to the first plane face;

the laterally-compliant annulus is disposed between the inwardly-extended part of the second plane face of the rigid annulus and the axially-extended part of the seal body.]

[22. The apparatus of claim 13, wherein the laterally-compliant annulus is corrugated and is disposed between the rigid annulus and a part of the seal body substantially co-planar with the rigid annulus and the instrument seal.]

[23. The apparatus of claim 22, wherein:

the laterally-compliant annulus and the instrument seal are provided by an outer radial zone and an inner radial zone, respectively, of a single seal molding; and the single seal molding additionally includes:

a rigid annulus anchor radial zone extending between the inner radial zone and the outer radial zone, the rigid annulus being attached to the rigid annulus anchor radial zone, and an anchoring radial zone extending outwards from the outer radial zone, the anchoring radial zone being attached to the seal body.]

[24. The apparatus of claim 23, wherein:

the rigid annulus anchor radial zone extends axially on opposite sides of the seal molding;

the rigid annulus includes a first rigid annulus half and a second rigid annular half, each rigid annulus half having a plane face wherein an annular groove is formed; and a rigid annulus half is mounted on each side of the seal molding with the rigid annulus anchor radial zone engaging in the annular groove of the rigid annulus half.]

[25. The apparatus of claim 22, wherein:

the seal body includes a first internal face opposite a second internal face, the internal faces being disposed about the bore; and the rigid annulus is slidably mounted between the first internal face and the second internal face.]

[26. The apparatus of claim 25, wherein:

the laterally-compliant annulus and the instrument seal are provided by an outer radial zone and an inner radial zone, respectively, of a single seal molding; and the single seal molding additionally includes:

extending between the inner radial zone and the outer radial zone, a rigid annulus anchor radial zone whereto the rigid annulus is attached, and an anchoring radial zone extending outwards from the outer radial zone and attached to the seal body.]

[27. The apparatus of claim 26, additionally comprising a low-friction coating applied to the seal molding.]

[28. The apparatus of claim 26, wherein:

the rigid annulus anchor radial zone extends axially on opposite sides of the seal molding;

the rigid annulus includes a first rigid annulus half and a second rigid annular half, each rigid annulus half having a plane face wherein an annular groove is formed; and a rigid annulus half is mounted on each side of the seal molding with the rigid annulus anchor radial zone engaging in the annular groove of the rigid annulus half.]

[29. The apparatus of claim 28, additionally comprising a pin passing through the first rigid annulus half, the rigid annulus anchor radial zone, and the second rigid annulus half.]

[30. The apparatus of claim 26, wherein:

the seal body comprises:

a cap including the first internal face and a curved side having an inner annular step and an outer annular step formed therein, and a base including the second internal face, the second internal face having an annular step formed therein; and the base fits into the cap such that:

the base engages with the outer annular step to define a spacing between the rigid annulus and the internal faces of the seal body, and the annular step in the base and the inner annular step in the cap form an annular groove sealing with the anchoring radial zone of the seal molding.]

[31. The apparatus of claim 26, wherein:

the seal body comprises:

a cap including the first internal face and a curved side having an edge, and a base including the second internal face and having an inner annular step and an outer annular step formed therein; and the base fits into the cap such that:

the edge of the cap engages with the outer annular step in the base to define a spicing between the rigid annulus and the internal faces of the seal body, and the annular step in the cap and the inner annular step in the base form an annular groove sealing with the anchoring radial zone of the seal molding.]

32. The apparatus of claim 1, additionally comprising a low friction coating applied to the instrument seal.

[33. The apparatus of claim 1, additionally comprising a lateral force transmitting means for transmitting a lateral force from the instrument directly to the laterally-compliant seal mounting means to move the instrument seal laterally with a reduced lateral force between the instrument and the instrument port.]

[34. The apparatus of claim 33, wherein:

the laterally-compliant seal mounting means includes a rigid annulus slidably mounted relative to the seal body;

the instrument seal is attached to the rigid annulus with the instrument port inside the annulus;

the lateral force transmitting means is mounted on the rigid annulus; and the lateral force transmitting means comprises plural radially-acting means, disposed about the instrument port and biassed towards the instrument port, for contacting the instrument to transmit the lateral force from the instrument to the rigid annulus.]

[35. The apparatus of claim 34, wherein the plural radially-acting means are disposed substantially symmetrically about the instrument port.]

[36. The apparatus of claim 34, wherein each radially-acting means includes a buffer slidably mounted on the rigid annulus, the buffer being spring-loaded towards the instrument port.]

[37. The apparatus of claim 34, wherein each radially-acting means includes a spring member attached to the rigid annulus in a radially-offset manner such that a part of the spring member remote from the rigid annulus is biassed towards the instrument port.]

[38. The apparatus of claim 37, wherein each radially-acting means additionally includes a paddle attached to the part of the spring member remote from the rigid annulus.]

[39. The apparatus of claim 37, wherein each radially-acting means additionally includes a roller rotatably mounted on the part of the spring member remote from the rigid annulus.]

[40. The apparatus of claim 34, wherein each radially-acting means includes:

a member pivotally mounted on the rigid annulus; and a means for biassing a part of the member remote from the rigid annuls towards the instrument port.]

[41. The apparatus of claim 40, wherein each radially-acting means additionally includes a paddle attached to the part of the member remote from the rigid annulus.]

[42. The apparatus of claim 40, wherein each radially-acting means additionally includes a roller rotatably mounted on the part of the member remote from the rigid annulus.]

43. Apparatus for use in a surgical instrument to provide a gas-tight seal with an instrument passed through the seal, the instrument having a diameter in a wide range of diameters, the apparatus comprising:

a seal body including a bore wherethrough the instrument is passed, the bore defining an axis;

a rigid mounting having a bore;

an instrument seal of an elastic material, the instrument seal:

including an instrument port wherethrough the instrument is passed, being substantially perpendicular to the axis, and being attached to the rigid mounting with the instrument port over the bore of the rigid mounting; and a compliant mounting means for mounting the rigid mounting in the seal body, the mounting means permitting the rigid mounting to move freely laterally and restricting axial movement of the rigid mounting relative to the seal body, *wherein no provision is made for anchoring the rigid mounting to the seal body*.

44. The apparatus of claim 43, wherein:

[the compliant mounting means includes a first internal face formed in the seal body opposite a second internal face, the internal faces being disposed about the bore; and]

the rigid mounting is slidably mounted between [the] *a* first internal face and [the] *a* second internal face [formed in] *of* the seal body.

[45. The apparatus of claim 44, wherein:

the rigid mounting includes a first plane face opposite a second plane face; and the compliant mounting means additionally includes:

a first annular wiper attached to the first plane face of the rigid mounting and contacting the first internal face formed in the seal body; and a second annular wiper attached to the second plane face of the rigid mounting and contacting the second internal face formed in the seal body.]

[46. The apparatus of claim 43, wherein the compliant mounting means includes a compliant annulus disposed between the rigid mounting and the seal body.]

[47. The apparatus of claim 46, wherein the compliant annulus is corrugated and is disposed between the rigid mounting and a part of the seal body axially displaced from the rigid mounting and the instrument seal.]

[48. The apparatus of claim 46, wherein the compliant annulus is corrugated and is disposed between the rigid mounting and a part of the seal body substantially coplanar with the rigid mounting and the instrument seal.]

[49. The apparatus of claim 48, wherein:

the compliant annulus and the instrument seal are provided by an outer zone and an inner zone, respectively, of a single seal molding; and the single seal molding additionally includes:

a rigid mounting anchor zone extending between the inner zone and the outer zone, the rigid mounting being attached to the rigid mounting anchor zone, and an anchoring zone extending outwards from the outer zone, the anchoring zone being attached to the seal body.]

[50. The apparatus of claim 49, wherein:

the rigid mounting anchor zone extends axially on opposite sides of the seal molding;

the rigid mounting includes a first rigid mounting half and a second rigid mounting half, each rigid mounting half having a face wherein a groove is formed: and a rigid mounting half is mounted on each side of the seal molding with the rigid mounting anchor zone engaging in the groove in the rigid mounting half.]

51. The apparatus of claim 43, additionally comprising a lateral force transmitting means for transmitting a lateral force from the instrument directly to the rigid mounting to move the instrument seal laterally with a reduced lateral force between the instrument and the instrument port.

52. The apparatus of claim 51, wherein:

the lateral force transmitting means is mounted on the rigid mounting; and the lateral force transmitting means comprises plural radially-acting means, disposed about the instrument port and biassed towards the instrument port, for contacting the instrument to transmit the lateral force from the instrument to the rigid mounting.

53. The apparatus of claim 43, additionally comprising a low-friction coating applied to the instrument seal.

[54. A seal for use in a surgical instrument to provide a gas-fight seal with an instrument passed through the seal, the instrument having a diameter in a wide range of diameters, the seal comprising:

a seal body including:

a bore wherethrough the instrument is passed, the bore defining an axis, a first internal face opposite a second internal face, the internal faces being disposed about the bore;

a rigid annulus slidably mounted between the first internal face and the second internal face; and a seal molding of an elastic material, the seal molding being disposed within the seal body substantially perpendicular to the axis, and including:

an inner zone providing an instrument seal and including an instrument port wherethrough the instrument is passed, a corrugated, laterally compliant, outer zone, a rigid annulus anchor zone extending between the inner zone and the outer zone, the rigid annulus being attached to the rigid annulus anchor zone, and an anchoring zone extending outwards from the outer zone, the anchoring zone being attached to the seal body.]

[55. The seal of claim 54, wherein the seal body comprises:

a cap including the first internal face and a curved side having an annular step formed therein; and a base including the second internal face, the base fitting into the cap and engaging with the annular step to define a spacing between the rigid annulus and the internal faces of the seal body.]

[56. The seal of claim 54, wherein the seal body comprises:

a cap including the first internal face and a curved side having an edge; and a base including the second internal face and an annular step, the base fitting into the cap such that the edge of the cap engages with the annular step to define a spacing between the rigid annulus and the internal faces of the seal body.]

[57. The seal of claim 54, additionally comprising a lateral force transmitting means for transmitting a lateral force from the instrument directly to the rigid annulus to move the instrument seal laterally with a reduced lateral force between the instrument and the instrument port.]

[58. The seal of claim 54, additionally comprising a low-friction coating applied to the seal molding.]

*59. The apparatus of claim 1, wherein the rigid annulus is slidably mounted within the seal body, and wherein at least one wiper is located between the rigid annulus and the seal body.*

*60. The apparatus of claim 59, wherein the at least one wiper extends from the rigid annulus in a generally axial direction.*

*61. The apparatus of claim 7, wherein the instrument port is located entirely between the first and second plane faces of the rigid annulus.*

*62. The apparatus of claim 8, wherein the first annular wiper and the second annular wiper project from the rigid annulus in generally axial directions.*

*63. The apparatus of claim 1, wherein the seal body includes a first internal face opposite a second internal face, the internal faces being disposed about the bore, and wherein the rigid annulus includes a first face and a second face, and the rigid annulus is positioned in the seal body with the first face opposite the first internal face of the seal body and the second face opposite the second internal face of the seal body, and wherein the rigid annulus is slidably mounted between the first internal face and the second internal face.*

*64. The apparatus of claim 63, wherein the instrument seal assembly additionally includes:*

*a first wiper attached to the first face of the rigid annulus and contacting the first internal face of the seal body; and*

*a second wiper attached to the second face of the rigid annulus and contacting the second internal face of the seal body.*

*65. The apparatus of claim 1, wherein the rigid annulus is slidably mounted within the seal body, and wherein at least one wiper seals between the rigid annulus and the seal body.*

*66. The apparatus of claim 1, wherein the seal body includes a first internal face opposite a second internal face, the internal faces being disposed about the bore, and wherein the rigid annulus interacts with the internal faces of the seal body to limit the degree of axial movement of the instrument seal and to allow the instrument seal to move freely laterally in response to lateral movement of the instrument.*

*67. The apparatus of claim 1, wherein the instrument seal assembly is axially restricted in that the instrument seal is generally held in position axially when an instrument is inserted into or withdrawn from the instrument port.*

*68. The apparatus of claim 67, wherein at least a portion of the instrument seal assembly slidingly seals against the seal body.*

*69. The apparatus of claim 1, wherein at least a portion of the instrument seal assembly slidingly seals against the seal body.*

*70. The apparatus of claim 1, wherein the instrument seal assembly does not comprise a corrugated seal.*

*71. The apparatus of claim 1, wherein the instrument seal assembly moves within a defined range of motion inside the seal body.*

*72. The apparatus of claim 71, wherein the defined range of motion lies within a plane.*

*73. The apparatus of claim 71, wherein at least one wiper is located between the rigid annulus and the seal body.*

*74. The apparatus of claim 1, wherein the instrument seal accommodates instruments within a range of diameters from 4 mm to 12 mm.*

*75. The apparatus of claim 43, wherein the rigid mounting is slidably mounted within the seal body, and wherein at least one wiper is located between the rigid mounting and the seal body.*

*76. The apparatus of claim 43, wherein the instrument seal accommodates instruments within a range of diameters from 4 mm to 12 mm.*

*77. Apparatus for use in a surgical instrument to provide a gas-tight seal with an instrument passed through the seal, the instrument having a diameter in a wide range of diameters, the apparatus comprising:*

*a seal body including a bore wherethrough the instrument is passed, the bore defining an axis; and*

*an instrument seal assembly, including:*

*a rigid annulus, and*

*an instrument seal of an elastic material, the instrument seal: including an instrument port wherethrough the instrument is passed; and*

*being attached to the rigid annulus with the instrument port inside the annulus,*

*the instrument seal assembly being mounted in the seal body in a manner restricting axial movement of the instrument seal assembly along the axis and permitting free lateral movement of the instrument seal assembly within a defined range of motion in response to movement of the instrument passed through the instrument port, wherein at least a portion of the instrument seal assembly slidingly seals against the seal body, no provision is made for anchoring a portion of the instrument seal assembly to the seal body, and the instrument seal assembly does not comprise a corrugated seal.*

*78. The apparatus of claim 77, wherein the rigid annulus is slidably mounted within the seal body, and wherein at least one wiper seals between the rigid annulus and the seal body.*

*79. The apparatus of claim 77, wherein the seal body includes a first internal face opposite a second internal face, the internal faces being disposed about the bore, and wherein the rigid annulus includes a first face and a second face, and the rigid annulus is positioned in the seal body with the first face opposite the first internal face of the seal body and the second face opposite the second internal face of the seal body, and wherein the rigid annulus is slidably mounted between the first internal face and the second internal face.*

*80. The apparatus of claim 79, wherein the instrument seal assembly additionally includes:*

*a first wiper attached to the first face of the rigid annulus and contacting the first internal face of the seal body; and*

*a second wiper attached to the second face of the rigid annulus and contacting the second internal face of the seal body.*

*81. The apparatus of claim 77, wherein the rigid annulus is slidably mounted within the seal body, and wherein at least one wiper is located between the rigid annulus and the seal body.*

*82. The apparatus of claim 77, wherein the instrument seal accommodates instruments within a range of diameters from 4 mm to 12 mm.*

*83. Apparatus for use in a surgical instrument to provide a gas-tight seal with an instrument passed through the seal, the instrument having a diameter in a wide range of diameters, the apparatus comprising:*

*a seal body including a bore wherethrough the instrument is passed, the bore defining an axis; and*

*an instrument seal assembly, including:*

*a rigid annulus, and*

*an instrument seal of an elastic material, the instrument seal: including an instrument port wherethrough the instrument is passed; and*

*being attached to the rigid annulus with the instrument port inside the annulus,*

*the instrument seal assembly being mounted in the seal body in a manner restricting axial movement of the instrument seal assembly along the axis such that the seal body limits the degree of movement of the instrument seal along the axis, and in a manner permitting free lateral movement of the instrument seal assembly within a defined range of motion in response to movement of the instrument passed through the instrument port, wherein no provision is made for anchoring the instrument seal assembly to the seal body.*

*84. The apparatus of claim 83, wherein the seal body includes a first internal face opposite a second internal face, the internal faces being disposed about the bore, and wherein the rigid annulus interacts with the internal faces of the seal body to restrict axial movement of the instrument seal and to allow the instrument seal to move freely laterally in response to lateral movement of the instrument.*

*85. The apparatus of claim 83, wherein the rigid annulus is slidably mounted within the seal body, and wherein at least one wiper is located between the rigid annulus and the seal body.*

*86. The apparatus of claim 83, wherein the instrument seal accommodates instruments within a range of diameters from 4 mm to 12 mm.*

*87. Apparatus for use in a surgical instrument to provide a gas-tight seal with an instrument passed through the seal, the instrument having a diameter in a wide range of diameters, the apparatus comprising:*

*a seal body including a bore wherethrough the instrument is passed, the bore defining an axis; and*

*an instrument seal assembly, including:*

*a rigid annulus, and*

*an instrument seal of an elastic material, the instrument seal: including an instrument port wherethrough the instrument is passed; and*

*being attached to the rigid annulus with the instrument port inside the annulus,*

*the instrument seal assembly being mounted in the seal body in a manner restricting axial movement of the instrument seal assembly along the axis and permitting free lateral movement of the instrument seal assembly within a defined range of motion in response to movement of the instrument passed through the instrument port, wherein the instrument seal assembly is laterally compliant in that the instrument seal moves laterally in response to lateral movement of the instrument passed through the instrument port and is axially restricted in that the instrument seal is generally held in position axially when an instrument is inserted into or withdrawn from the instrument port, and wherein no provision is made for anchoring the instrument seal assembly to the seal body.*

*88. The apparatus of claim 87, wherein at least a portion of the instrument seal assembly slidingly seals against the seal body.*

*89. The apparatus of claim 87, wherein the rigid annulus is slidably mounted within the seal body, and wherein at least one wiper is located between the rigid annulus and the seal body.*

*90. The apparatus of claim 87, wherein the instrument seal accommodates instruments within a range of diameters from 4 mm to 12 mm.*

*91. Apparatus for use in a surgical instrument to provide a gas-tight seal with an instrument passed through the seal, the instrument having a diameter in a wide range of diameters, the apparatus comprising:*

*a seal body including a bore wherethrough the instrument is passed, the bore defining an axis; and*

*an instrument seal assembly, including:*

*a rigid annulus, and*

*an instrument seal of an elastic material, the instrument seal: including an instrument port wherethrough the instrument is passed; and*

*being attached to the rigid annulus with the instrument port inside the annulus,*

*the instrument seal assembly being mounted in the seal body in a manner restricting the instrument seal assembly from moving along the axis and permitting the instrument port of the instrument seal to move to and from the axis within a defined range of motion in response to movement of the instrument passed through the instrument port, wherein no provision is made for anchoring the instrument seal assembly to the seal body.*

*92. The apparatus of claim 91, wherein at least a portion of the instrument seal assembly slidingly seals against the seal body.*

*93. The apparatus of claim 91, wherein the instrument seal assembly does not comprise a corrugated seal.*

*94. The apparatus of claim 91, wherein the defined range of motion lies within a plane.*

*95. The apparatus of claim 91, wherein the rigid annulus is slidably mounted within the seal body, and wherein at least one wiper is located between the rigid annulus and the seal body.*

*96. The apparatus of claim 91, wherein the instrument seal accommodates instruments within a range of diameters from 4 mm to 12 mm.*

* * * * *